US007759306B2

(12) United States Patent
Simoni et al.

(10) Patent No.: US 7,759,306 B2
(45) Date of Patent: Jul. 20, 2010

(54) METHODS OF TREATING ACUTE BLOOD LOSS

(76) Inventors: Jan S. Simoni, 5102 80th, Condo 214, Lubbock, TX (US) 79424; Grace Simoni, 5102 80th, Condo 214, Lubbock, TX (US) 79424; Mario J. Feola, 131 N. Utica Ave., Lubbock, TX (US) 79416

( * ) Notice: Subject to any disclaimer, the term of this patent is extended or adjusted under 35 U.S.C. 154(b) by 0 days.

(21) Appl. No.: 11/436,089

(22) Filed: May 16, 2006

(65) Prior Publication Data

US 2007/0270333 A1 Nov. 22, 2007

(51) Int. Cl.
*A61K 38/42* (2006.01)
*C07K 14/00* (2006.01)
(52) U.S. Cl. .......................................... 514/6; 530/385
(58) Field of Classification Search ....................... None
See application file for complete search history.

(56) References Cited

U.S. PATENT DOCUMENTS

| | | |
|---|---|---|
| 4,598,064 A | 7/1986 | Walder |
| 4,600,531 A | 7/1986 | Walder |
| 4,826,811 A | 5/1989 | Sehgal et al. |
| 4,831,012 A | 5/1989 | Estep |
| 4,857,636 A | 8/1989 | Hsia |
| 5,028,588 A | 7/1991 | Hoffman et al. |
| 5,084,558 A | 1/1992 | Rausch et al. |
| 5,194,590 A | 3/1993 | Sehgal et al. |
| 5,281,579 A | 1/1994 | Estep |
| 5,296,465 A | 3/1994 | Rausch et al. |
| 5,439,882 A | 8/1995 | Feola et al. |
| 5,464,814 A | 11/1995 | Sehgal et al. |
| 5,563,254 A | 10/1996 | Hoffman et al. |
| 5,631,219 A | 5/1997 | Rosenthal et al. |
| 5,661,124 A | 8/1997 | Hoffman et al. |
| 5,753,616 A | 5/1998 | Rausch et al. |
| 5,895,810 A | 4/1999 | Light et al. |
| 6,022,849 A | 2/2000 | Olson et al. |
| 6,133,425 A | 10/2000 | Sehgal et al. |
| 6,323,320 B1 | 11/2001 | Sehgal et al. |
| 6,432,927 B1 | 8/2002 | Gregory et al. |
| 6,562,799 B1 | 5/2003 | Semenza |
| 6,838,430 B2 | 1/2005 | Arbeit |
| 6,849,718 B2 | 2/2005 | Kaelin, Jr. et al. |
| 6,914,127 B2 | 7/2005 | Sehgal et al. |
| 2002/0120098 A1 | 8/2002 | Bell et al. |
| 2004/0242464 A1 | 12/2004 | Tye |

OTHER PUBLICATIONS

Yeh and Alayash,"Redox side reactions of haemoglobin and cell signalling mechanisms", Journal of Internal Medicine 253: 518-526 (2003).*
Shafi and Kauder, "Fluid Resuscitation and Blood Replacement in Patients with Polytrauma", Clinical Orthopaedics and Related Research, No. 422: 37-42, Lippincott, Williams & Wilkins (2004).*

Amberson et al., 1934, "On the use of Ringer-Locke solutions containing hemoglobin as a substitute for normal blood in mammals," J. Cell. Compar. Physiol. 5:359-382.
Amberson et al., 1937, "Blood Substitutes," Biol. Rev. 12:48-86.
Amberson et al., 1949, "Clinical Experience with Hemoglobin-Saline Solutions," J. Appl. Physiol. 1: 469-489.
Adamson, 1991, "Erythropoietin: its role in the regulation of erythropoiesis and as a therapeutic in humans," Biotechnology 19:351-63.
Alayash, 2004, "Oxygen therapeutics: can we tame haemoglobin?," Nat. Rev. Drug Discov. 3(2):152-9.
Allison et al., 2004, "Successful use of a polymerized hemoglobin blood substitute in a critically anemic Jehovah's Witness," South. Med. J. 97(12):1257-8.
Balla et al., 1995, "Endothelial cell heme oxygenase and ferritin induction in rat lung by hemoglobin in vivo," Am. J. Physiol. 268(2 Pt 1):L321-7.
Blumberg et al., 1996, "A cost analysis of autologous and allogeneic transfusions in hip-replacement surgery," Am. J. Surg. 171(3):324-30.
Bonnet et al., 1995, "Surgical risk factors for severe postoperative proliferative vitreoretinopathy (PVR) in retinal detachment with grade B PVR," Graefes. Arch. Clin. Exp. Ophthalmol. 233(12):789-91.
Brines et al., 2005, "Emerging biological roles for erythropoietin in the nervous system," Nat. Rev. Neurosci. 6(6):484-94.
Campbell, 2004, "Pathophysiology of Anaemia," Nursing Times 100(47): 40-43.
Cheung et al., 2001, "The effects of hemoglobin glutamer-200 (bovine) on the microcirculation in a canine hypovolemia model: a noninvasive computer-assisted intravital microscopy study," Anesth. Analg. 93(4):832-8.
D'Agnillo et al., 2001, "Redox cycling of diaspirin cross-linked hemoglobin induces G2/M arrest and apoptosis in cultured endothelial cells," Blood 98(12):3315-23.

(Continued)

*Primary Examiner*—Anand U Desai
(74) *Attorney, Agent, or Firm*—Jones Day

(57) ABSTRACT

The present invention relates to novel methods of using blood substitutes to treat acute blood loss and novel pharmaceutical compositions comprising blood substitutes. Blood substitutes useful for the methods of the present invention can (1) induce expression of erythropoietin as tested in a cell culture under normoxic conditions, and/or (2) induce erythropoiesis under normoxic conditions as measured by (a) a decrease in the doubling time of the subject's hematocrit or hemoglobin, and/or (b) an increase in the subject's circulating erythropoietin level. Blood substitutes useful for the pharmaceutical compositions of the present invention can (1) stabilize HIF-1 alpha expression, and/or (2) down regulate NF-kappa B. Preferably, the blood substitutes are cross-linked hemoglobin blood substitutes, or more preferably, cross-linked hemoglobins that comprise a hemoglobin that is cross-linked intramolecularly with periodate-oxidized ATP, cross-linked intermolecularly with periodate-oxidized adenosine, and conugated with reduced glutathione.

20 Claims, 7 Drawing Sheets

OTHER PUBLICATIONS

Dolznig et al., 2002, "Apoptosis protection by the Epo target Bcl-X(L) allows factor-independent differentiation of primary erythroblasts," Curr. Biol. 12(13):1076-85.

Feola et al., 1988, "Complement activation and the toxicity of stroma-free hemoglobin solutions in primates," Circ. Shock 25(4):275-90.

Feola et al., 1988, "Toxicity of polymerized hemoglobin solutions," Surg. Gynecol. Obstet. 166(3):211-22.

Feola et al., 1992, "Clinical trial of a hemoglobin based blood substitute in patients with sickle cell anemia," Surg. Gynecol. Obstet. 174(5):379-86.

Flanders et al., 1998, "Transforming growth factor-βs in neurodegenerative disease," Prog. Neurobiol. 54(1):71-85.

Friedman et al., 1996, "The risk of hemorrhage after radiosurgery for arteriovenous malformations," J Neurosurg. 84(6):912-9.

Gannon et al., 2002, "Severe anemia after gastrointestinal hemorrhage in a Jehovah's Witness: new treatment strategies," Severe anemia after gastrointestinal hemorrhage in a Jehovah's Witness: new treatment strategies, Crit. Care. Med. 30(8):1893-5.

Gawryl, 2003, "Hemopure®: Clinical Development and Experience," The 9th International Symposium in Blood Substitute Program, 46.

Gilmore, 2005, http://people.bu.edu/gilmore/nf-kb/inducers/.

Gleadle et al., 1997, "Induction of hypoxia-inducible factor-1, erythropoietin, vascular endothelial growth factor, and glucose transporter-1 by hypoxia: evidence against a regulatory role for Src kinase," Blood 89(2):503-9.

Gleadle et al., 1998, "Hypoxia and the regulation of gene expression," Mol. Med. Today 4(3):122-9.

Goldman et al., 1998, "Acellular hemoglobin-mediated oxidative stress toward endothelium: a role for ferryl iron," Am. J. Physiol. 275(3 Pt 2):H1046-53.

Guglielmi et al., 1992, "Endovascular treatment of posterior circulation aneurysms by electrothrombosis using electrically detachable coils," J. Neurosurg. 77(4):515-24.

Haddad et al., 2000, "Antioxidant/pro-oxidant equilibrium regulates HIF-1alpha and NF-kappa B redox sensitivity. Evidence for inhibition by glutathione oxidation in alveolar epithelial cells," J. Biol. Chem. 275(28):21130-9.

Haddad et al., 2001, "A non-hypoxic, ROS-sensitive pathway mediates TNF-alpha-dependent regulation of HIF-1alpha," FEBS Lett. 505(2):269-74.

Hawkins, 1999, "Blood-bank debt. Surgeries are postponed as shortages grow critical in a changing blood-donor business," US News World Rep. 126(3):34.

Hayes et al., 2001, "A double-blind study to evaluate the safety of recombinant human hemoglobin in surgical patients during general anesthesia," J. Cardiothorac. Vasc. Anesth. 15(5):593-602.

Hellwig-Bürgel et al., 1999, "Interleukin-1beta and tumor necrosis factor-alpha stimulate DNA binding of hypoxia-inducible factor-1," Blood 94(5):1561-7.

Hess et al., 1994, "Increased vascular resistance with hemoglobin-based oxygen carriers," Artif. Cells Blood Substit. Immobil. Biotechnol. 22(3):361-72.

Hillman et al., 1996, "Red Cell Manual," 7th Ed., Philadelphia: F.A. Davis, viii, pp. 190.

Hoots et al., 2001, "The impact of Creutzfeldt-Jakob disease and variant Creutzfeldt-Jakob disease on plasma safety," Transfus. Med. Rev. 15(2 Suppl 1):45-59.

Hunt et al., 1968, "Surgical risk as related to time of intervention in the repair of intracranial aneurysms," J Neurosurg. 28(1):14-20.

Kallio et al., 1999, "Regulation of the hypoxia-inducible transcription factor 1alpha by the ubiquitin-proteasome pathway," J. Biol. Chem. 274(10):6519-25.

Kasper et al., 1996, "Effects of a hemoglobin-based oxygen carrier (HBOC-201) on hemodynamics and oxygen transport in patients undergoing preoperative hemodilution for elective abdominal aortic surgery," Anesth. Analg. 83(5):921-7.

Kasper et al., 1998, "The effects of increased doses of bovine hemoglobin on hemodynamics and oxygen transport in patients undergoing preoperative hemodilution for elective abdominal aortic surgery," Anesth. Analg. 87(2):284-91.

Klein, 2005, "Blood substitutes: how close to a solution?," Dev. Biol. (Basel). 120:45-52.

Lacombe et al., 1998, "Biology of erythropoietin," Haematologica 83(8):724-32.

Lando et al., 2000, "A redox mechanism controls differential DNA binding activities of hypoxia-inducible factor (HIF) 1alpha and the HIF-like factor," J. Biol. Chem. 275(7):4618-27.

Lanzinger et al., 2005, "Use of hemoglobin raffimer for postoperative life-threatening anemia in a Jehovah's Witness," Can. J. Anaesth. 52(4):369-73.

Linch, 1989, "The regulation of erythropoiesis in man," Schweiz. Med. Wochenschr. 119(39):1327-8.

Liu et al., 2003, "Erythroid gene suppression by NF-κ B," J. Biol. Chem. 278(21):19534-40.

Lutton et al., 1999,"Pharmacologic effects of the red blood cell substitutes cross-linked and non-cross-linked hemoglobins on hematopoiesis in rabbits," Pharmacology 58(6):319-24.

Matkovic et al., 1991, "Surgical risk of hemorrhage in cerebral amyloid angiopathy," Stroke 22(4):456-61.

Mayberg et al., 1994, "Guidelines for the management of aneurysmal subarachnoid hemorrhage. A statement for healthcare professionals from a special writing group of the Stroke Council, American Heart Association," Stroke 25(11):2315-28.

Meguro et al., 2001, "Oxyhemoglobin induces caspase-mediated cell death in cerebral endothelial cells," J. Neurochem. 77(4):1128-35.

Merck Manual of Diagnosis and Therapy, John Wiley & Sons, 17th ed., Mar. 1, 1999, Section 1: Nutritional Disorders, Chapter 3: Vitamin Deficiency, Dependency, and Toxicity, pp. 42.

Merck Manual of Diagnosis and Therapy, John Wiley & Sons, 17th ed., Mar. 1, 1999, Section 11: Hematology and Oncology, Chapter 127: Anemias, pp. 849-850, 854.

Mohara et al., 2005, "Effects of nutrient and hemoglobin enriched cell free perfusates upon ex vivo isolated rat heart preparation," ASAIO J. 51(3):288-95.

Moqattash et al., 1997, "Effect of blood substitute, recombinant hemoglobin, on in vivo hematopoietic recovery from AZT toxicity," Acta. Haematol. 98(2):76-82.

Moore, 2003, "Blood substitutes: the future is now," J. Am. Coll. Surg. 196(1):1-17.

National Blood Data Resource Center, web pages, 2005, www.nbdrc.org.

North Central Blood Services, web pages, 2005, www.yourbloodcenter.org.

OH et al., 1999, "Cytokine regulation of CC and CXC chemokine expression by human astrocytes," J. Neurovirol. 5(1):82-94.

Pahl, 1999, "Activators and target genes of Rel/NF-kappaB transcription factors," Oncogene 18(49):6853-66.

Quick et al., 1953, "Hemophilic condition in a girl," AMA Am. J. Dis. Child 85(6):698-705.

Reiss, 2001, "Oxygen Carriers ("Blood Substitutes")-Raison d'Etre, Chemistry, and Some Physiology Blut ist ein ganz besondrer Saft 1," Chem. Rev. 2797.

Richard et al., 1999, "p42/p44 mitogen-activated protein kinases phosphorylate hypoxia-inducible factor 1alpha (HIF-1alpha) and enhance the transcriptional activity of HIF-1," J. Biol. Chem. 274(46):32631-7.

Rodriguez et al., 1990, "Colonic lipoma as a source of massive hemorrhage. Report of a case," Dis. Colon. Rectum. 33(11):977-9.

Sasaski, 2003, "Pleiotropic functions of erythropoietin," Intern. Med. 42(2):142-9.

Savitsky et al., 1978, "A clinical safety trial of stroma-free hemoglobin," Clin. Pharmacol. Ther. 23(1):73-80.

Schnipper et al., 2004, "Management of intracranial complications of sinus surgery," Otolaryngol Clin North Am. 37(2):453-72, ix.

Schreiber et al., 1996, "The risk of transfusion-transmitted viral infections. The Retrovirus Epidemiology Donor Study," N. Engl. J. Med. 334(26):1685-90.

Sellards et al., 1916, "Injection of hemoglobin in man and its relation to blood destruction, with special reference to the anemias," J. Med. Res. 34:469.

Semenza et al., 1992, "A nuclear factor induced by hypoxia via de novo protein synthesis binds to the human erythropoietin gene enhancer at a site required for transcriptional activation," Mol. Cell. Biol. 12(12):5447-54.

Shum et al., 1996, "The physiological and histopathological response of dogs to exchange transfusion with polyethylene glycol-modified bovine hemoglobin (PEG-Hb)," Artif. Cells Blood Substit. Immobil. Biotechnol. 24(6):655-83.

Simoni et al., 1990, "Generation of free oxygen radicals and the toxicity of hemoglobin solutions," Biomater. Artif. Cells Artif. Organs 18(2):189-202.

Simoni et al., 1994, "Cytokines and PAF release from human monocytes and macrophages: effect of hemoglobin and contaminants," Artif. Cells Blood Substit. Immobil. Biotechnol. 22(3):525-34.

Simoni et al., 1994, "Reaction of human endothelial cells to bovine hemoglobin solutions and tumor necrosis factor," Artif. Cells Blood Substit. Immobil. Biotechnol. 22(3):777-87.

Simoni et al., 1996, "An improved blood substitute. In vivo evaluation of its hemodynamic effects," ASAIO J. 42(5):M773-82.

Simoni et al., 1997, "Modified hemoglobin solution, with desired pharmacological properties, does not activate nuclear transcription factor NF-kappa B in human vascular endothelial cells," Artif. Cells Blood Substit. Immobil. Biotechnol. 25(1-2):193-210.

Simoni et al., 1997, "Expression of adhesion molecules and von Willebrand factor in human coronary artery endothelial cells incubated with differently modified hemoglobin solutions," Artif. Cells Blood Substit. Immobil. Biotechnol. 25(1-2):211-25.

Simoni et al., 1998, "Improved blood substitute: evaluation of its effects on human endothelial cells," ASAIO J. 44(5):M356-67.

Simoni et al., 2000, "A novel hemoglobin-adenosine-glutathione based blood substitute: evaluation of its effects on human blood ex vivo," ASAIO J. 46(6):679-92.

Simoni et al., 2002, "A novel hemoglboin-adensoine-glutathione based red cell substitute: its effects on human brain capillary endothelial cells," ASAIO J. 48(2):193.

Simoni et al., 2003, "Hemoglobin Transcriptional Activator and Suppressor. How to Tip the Balance?," The $9^{th}$ International Symposium on Blood Substitute Program, 69.

Simoni et al., 2003, "Activatory and Suppressive Roles of Hemoglobin-Based Blood Substitutes at Transcriptional Levels," ASAIO J. 49(2):181.

Simoni, 2005, "Artificial Oxygen Carrier—Its Front Line," Springer, 75-126.

Sirén et al., 2001, "Erythropoietin and erythropoietin receptor in human ischemic/hypoxic brain," Acta Neuropathol (Berl). 101(3):271-6.

Sloan et al., 1999, "Diaspirin cross-linked hemoglobin (DCLHb) in the treatment of severe traumatic hemorrhagic shock: a randomized controlled efficacy trial," JAMA 282(19):1857-64.

Socolovsky et al., 1999, "Fetal anemia and apoptosis of red cell progenitors in Stat5a-/-5b-/- mice: a direct role for Stat5 in Bcl-X(L) induction," Cell 98(2):181-91.

Surgenor et al., 1990, "Collection and transfusion of blood in the United States, 1982-1988," N. Engl. J. Med. 322(23):1646-51.

Trey et al., 1995, "The acute phase response and the hematopoietic system: the role of cytokines," Crit. Rev. Oncol. Hematol. 21(1-3):1-18.

Tsutsumi et al., 1999, "Risk of subarachnoid hemorrhage after surgical treatment of unruptured cerebral aneurysms," Stroke 30(6):1181-4.

Vairano et al., 2002, "Erythropoietin exerts anti-apoptotic effects on rat microglial cells in vitro," Eur. J. Neurosci. 16(4):584-92.

Van Wagoner et al., 1999, "Interleukin-6 (IL-6) production by astrocytes: autocrine regulation by IL-6 and the soluble IL-6 receptor," J. Neurosci. 19(13):5236-44.

Viele et al., 1997, "Recombinant human hemoglobin does not affect renal function in humans: analysis of safety and pharmacokinetics," Anesthesiology 86(4):848-58.

Wake et al., 1998, "Blood transfusion in developing countries: problems, priorities and practicalities," Trop. Doct. 28(1):4-8.

Wallace et al., 1993, "Collection and transfusion of blood and blood components in the United States, 1989," Transfusion 33(2):139-44.

Wang et al., 1993, "Characterization of hypoxia-inducible factor 1 and regulation of DNA binding activity by hypoxia," J. Biol. Chem. 268(29):21513-8.

Wang et al., 1995, "Purification and characterization of hypoxia-inducible factor 1," J. Biol. Chem. 270(3):1230-7.

Wenger, 2002, "Cellular adaptation to hypoxia: O2-sensing protein hydroxylases, hypoxia-inducible transcription factors, and O2-regulated gene expression," FASEB J. 16(10):1151-62.

Williams et al., 1977, Preservation and Clinical Use of Blood and Blood Componenets, Hematology, McGraw-Hill Book Company, New York.

Winslow, 1994, "Vasoconstriction and the efficacy of hemoglobin-based blood substitutes," Transfus. Clin. Biol. 1(1):9-14.

Winslow, 2000, "$\alpha\alpha$-crosslinked hemoglobin: was failure predicted by preclinical testing?," Vox Sang. 79(1):1-20.

Winslow, 2002, "Blood substitutes," Curr. Opin. Hematol. 9(2):146-51.

Winslow, 2003, "Current status of blood substitute research: towards a new paradigm," J. Intern. Med. 253(5):508-17.

Wirth, 1986, "Surgical treatment of incidental intracranial aneurysms," Clin. Neurosurg. 33:125-35.

Workshop on Criteria for Safety and Efficacy Evaluation of Oxygen Therapeutics and Red Cell Substitutes, Sep. 27-29, 1999, NIH, Bethesda, MD, Guidance for Industry, Criteria for Safety and Efficacy Evaluation of Oxygen Therapeutics as Red Cell Substitutes, 2004, U.S. Department of Health and Human Services, Food and Drug Administration, Center for Biologics Evaluation and Research, Rockville, MD.

World Health Organization Web Page, 2005, www.who.int.

Yeh et al., 2004, "Effects of cell-free hemoglobin on hypoxia-inducible factor (HIF-1alpha) and heme oxygenase (HO-1) expressions in endothelial cells subjected to hypoxia," Antioxid. Redox Signal. 6(6):944-53.

Yuen et al., 2005, "Quotidian nocturnal hemodialysis improves cytokine profile and enhances erythropoietin responsiveness," ASAIO J. 51(3):236-41.

Zucali et al. "Erythropoiesis and artificial blood substitution with a perfluorocarbon-polyol." J Lab Clin Med. Nov. 1979;94(5):742-6.

International Search Report for International Application No. PCT/US2007/011697.

Simoni, "Endothelial cell response to hemoglobin based oxygen carriers: Is the attenuation of pathological reactions possible?" A Supplemental Issue for The 13th Keio University International Symposium for Life Sciences and Medicine, Mar. 1, 2003, Plenary Lecture, pp. 30-31.

* cited by examiner

FIGURE 6
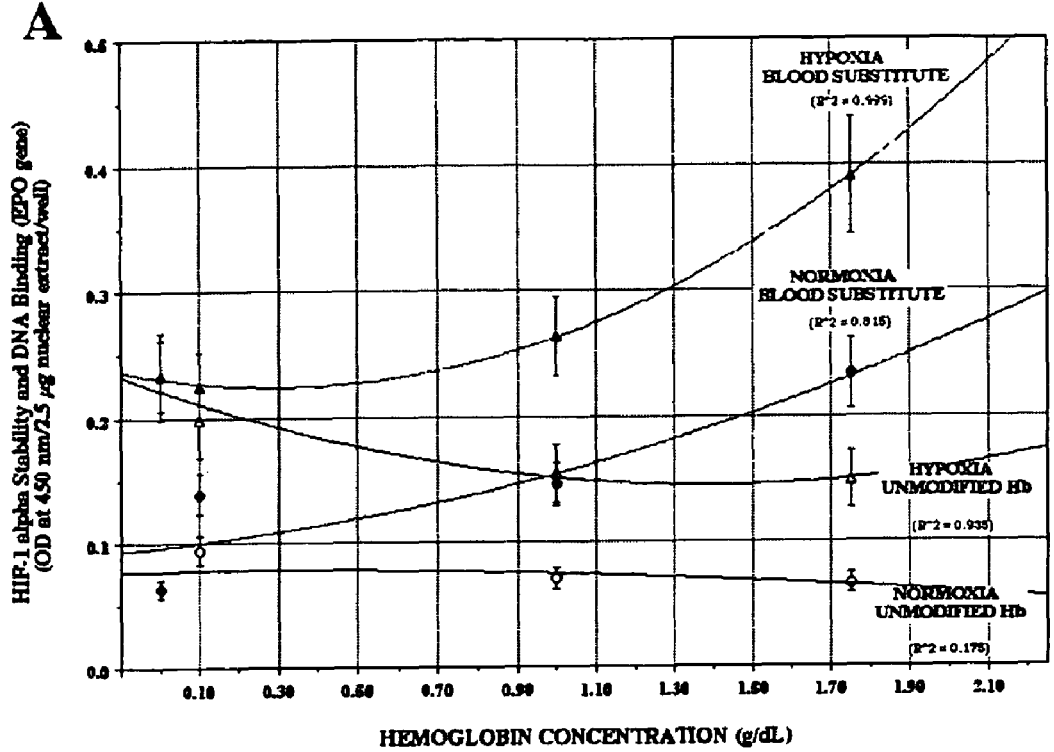
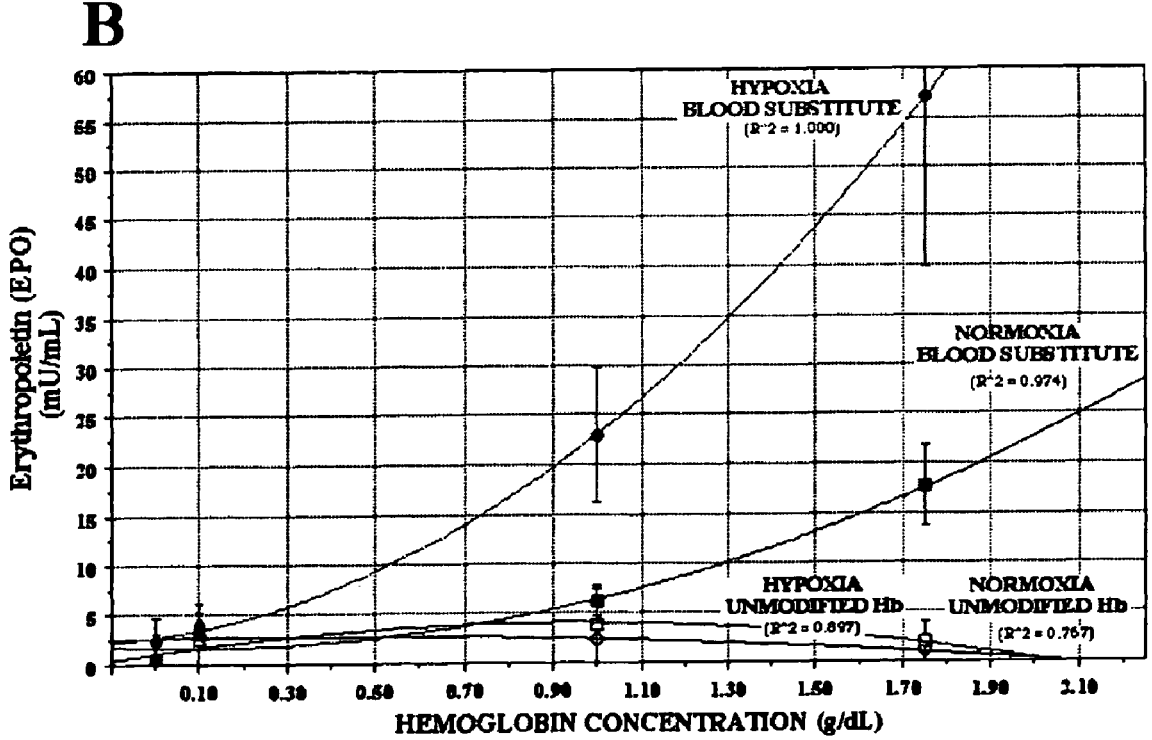

METHODS OF TREATING ACUTE BLOOD LOSS

1. INTRODUCTION

The present invention relates to novel methods for treating or preventing acute blood loss, preferably, acute blood loss anemia, or more preferably, anemia caused by (i) acute blood loss due to an illness, (ii) acute blood loss that occurs during surgery, or (iii) acute blood loss from trauma. The methods of the present invention comprise administering to subjects in need thereof a blood substitute in an amount effective to elevate blood volume and counter hypoxia associated with the acute blood loss, as well as induce erythropoiesis under normoxic conditions. In particular, the blood substitutes useful for the methods of the present invention are capable of (1) inducing expression of erythropoietin as tested in a cell culture under normoxic conditions, and/or (2) inducing erythropoiesis under normoxic conditions as measured by (a) a decrease in the doubling time of the subject's hematocrit or hemoglobin, or (b) an increase in the subject's circulating erythropoietin level.

The present invention also relates to novel pharmaceutical compositions comprising a therapeutically or prophylactically effective amount or volume of a cross-linked hemoglobin blood substitute in a pharmaceutically acceptable carrier, wherein the cross-linked hemoglobin blood substitute, when tested in a cell culture under normoxic conditions, induces expression of erythropoietin. The present invention further relates to novel pharmaceutical compositions comprising a therapeutically or prophylactically effective amount or volume of a cross-linked hemoglobin in a pharmaceutically acceptable carrier, wherein the cross-linked hemoglobin comprises a hemoglobin that is cross-linked intramolecularly with periodate-oxidized ATP, cross-linked intermolecularly with periodate-oxidized adenosine, and conjugated with reduced glutathione. The cross-linked hemoglobin blood substitutes and cross-linked hemoglobins useful for the pharmaceutical compositions of the present invention are capable of (1) stabilizing HIF-1 alpha expression, and/or (2) down regulating NF-kappa B, when tested in a cell culture.

2. BACKGROUND OF THE INVENTION

Even though the possibility of using cell-free hemoglobin (human and bovine) as a replacement for red blood cells has been considered since the late 19th century, it is only over the last few decades that concentrated efforts have been made in research on blood substitute. The main driving force behind this late effort was the concern regarding the potential transmission of blood borne infectious agents and a worldwide shortage of donor blood (Sellards et al. (1916) J Med Res 34:469; Amberson W R (1934) J Cell Compar Physiol 5:359-382; Amberson W R (1937) Biol Rev 12:48-86; Winslow R M (2002) Curr Opin Hematol 9(2):146-151; Winslow R M (2003) J Intern Med 253:508-517).

In the U.S., the implementation of sensitive screening tests has reduced the risk of infectious disease transmission to 1:63,000 blood transfusions for hepatitis B and 1:493,000 for HIV, with intermediate transmission rates for hepatitis C and human T-cell leukemia virus (Schreiber et al. (1996) N Engl J Med 334 (26):1685-1690). While the question of whether blood can transmit Creutzfeldt-Jacob's disease, or its bovine variant, is yet to be answered, there is still a dramatic improvement in blood safety in the developed world (Hoots et al. (2001) Transfus Med Rev 15(2 Suppl 1):45-59).

On the other hand, the lack of safety of the blood supply in the undeveloped world ought to concern the World Health Organization and the international scientific community on an urgent basis. In developing countries where the infected population is large, an estimated 6 million units of donated blood are not tested for HIV, hepatitis and syphilis (World Health Organization Web Page (2005); Wake et al (1998) Trop Doct 28(1):4-8).

The World Health Organization estimates a worldwide demand for 100 million units of blood per year; every 3.75 seconds a U.S. citizen requires a transfusion. At the same time, the rate of blood donors has fallen. Very often blood banks do not meet the demand because of low donation rates. The U.S. is already importing blood from Europe In the U.S., which annually uses approximately 12 million units, a shortage of 3-4 million units per year has been projected by the year 2030. This projected deficit of donated blood does not take into account the more acute need for blood in natural disasters, terrorist attacks and wars. While the demand for blood is increasing at a rate of 1% per year, U.S. blood donations are decreasing at an annual rate of 1% (Surgenor et al. (1990) N Engl J Med 322(23):1646-1651; Hawkins D. (1999) US News World Rep 126(3):34; National Blood Data Resource Center Web Page (2005); North Central Blood Services Web Page (2005)).

The cost of blood acquisition and testing has dramatically escalated. At present, the cost of collecting, testing and transfusing a unit of blood is about $1,000, and that is without factoring in the costs of lawsuits by those who received screened, but tainted blood (Blumberg et al. (1996) Am J Surg 171:324-330).

Another disadvantage of using red blood cells for transfusion is the fact that they must be kept refrigerated, and even then the packed cells have a shelf life of only 42 days. Also, their transfusion requires blood-typing and cross matching, which cannot be done at the scene of an accident or on a battlefield (Williams et al. (1977) Preservation and Clinical Use of Blood and Blood Components. Hematology. McGraw-Hill Book Company, New York).

2.1. Blood Substitutes

Because of these and other problems in transfusion medicine, it has become necessary to seek a new alternative in blood substitute. An effective blood substitute would eliminate the risk of transfusion-transmitted diseases and change the option available in managing the world's blood supply. A pathogen-free, universally compatible blood substitute without the need for cross matching would open a significant global market for both civilian and military applications. The implications of having a viable oxygen carrying solution are broad, starting with a potentially unlimited blood substitute free of any pathogens. A universal blood substitute could alter emergency treatment procedures for patients in hemorrhagic shock; be used in perioperative hemodilution during elective surgical procedures; prolong the survival time of organs donated for transplantation; improve the blood's oxygen carrying capacity to treat life threatening illnesses such as heart infarcts and strokes; be used in tumor radiosensitization; and in the treatment of anemia and other hematological disorders (Winslow R M. (2002) Curr Opin Hematol 9(2): 146-151).

In less than a decade, blood substitute research has moved from the realm of science fiction to reality. However, the commercial development of a usable blood substitute has been somewhat limited, and not yet successful. Though several different free hemoglobin based blood substitute have been developed, they have been proven unsatisfactory in limited human safety trials because of adverse side effects. The major problem with these products is their vasoconstrictor activity. Other reported problems have been the aggravation of oxidative stress and amplification of systemic inflammatory reactions (Workshop on Criteria for Safety and Efficacy Evaluation of Oxygen Therapeutics as Red Cell Substitutes (1999) NIH, Bethesda Md.; Winslow R M. (2000) Vox Sang 79(1): 1-20).

In fact, the commercial development of HEMASSIST™, Baxter Healthcare, Round Lake, Ill. (U.S. Pat. Nos. 4,598,064 and 4,600,531 to Walder; U.S. Pat. Nos. 4,831,012 and 5,281,579 to Estep) was halted, and the development of HEMOLINK™, a raffinose polymerized human hemoglobin solution, Hemosol, Mississauga, Canada (U.S. Pat. No. 4,857,636 to Hsia) was paused because of the high mortality rate or increase of myocardial infarction in humans. Earlier, the commercial development of OPTRO™, a recombinant Hb, Somatogen, Boulder, Colo. (U.S. Pat. Nos. 5,028,588, 5,563,254 and 5,661,124 to Hoffman et al.; U.S. Pat. No. 5,631,219 to Rosenthal et al.) was canceled because of the serious systemic inflammatory responses observed in the patients tested. HEMOPURE®, bovine glutaraldehyde polymerized hemoglobin solution, Biopure Inc., Cambridge, Mass. (U.S. Pat. Nos. 5,084,558, 5,296,465 and 5,753,616 to Rausch et al.; U.S. Pat. No. 5,895,810 to Light et al.), was put on clinical hold due to the "safety concerns." In 2002, Northfield Laboratories, Evanston, Ill. (U.S. Pat. Nos. 4,826,811, 5,194,590, 5,464,814, 6,133,425, 6,323,320, and 6,914,127 to Sehgal et al.) failed to get U.S. regulatory approval for its POLYHEME®, a glutaraldehyde polymerized human hemoglobin solution, used in elective surgery patients. Now, POLYHEME® is clinically tested on a compassionate use basis to treat severe hemorrhage of auto accident victims (Workshop on Criteria for Safety and Efficacy Evaluation of Oxygen Therapeutics as Red Cell Substitutes. Sep. 27-29, 1999. NIH, Bethesda, Md.; Simoni J. (2005) In: Artificial Oxygen Carrier. Its Front Line. K. Kobayashi et al. (Eds.). Springer-Verlag, Tokyo 2005 pp. 75-126; Moore E. (2003) J Am Coll Surgeons 196:1-17).

To be effective oxygen carrying plasma expanders, blood substitute must fulfill a number of requirements. In addition to being pathogen-free, non-toxic, non-immunogenic, and non-pyrogenic and having an extended shelf-life, these products should have a satisfactory oxygen carrying capacity close to that of whole blood, sufficient to permit effective tissue oxygenation and the circulatory retention time of at least 24 hours. The colloid osmotic pressure and viscosity of the blood substitute product should not exceed those of plasma (Workshop on Criteria for Safety and Efficacy Evaluation of Oxygen Therapeutics as Red Cell Substitutes (1999) NIH, Bethesda, Md.; Guidance for Industry. Criteria for Safety and Efficacy Evaluation of Oxygen Therapeutics as Red Cell Substitutes (2004) U.S. Department of Health and Human Services, Food and Drug Administration, Center for Biologies Evaluation and Research, Rockville, Md.).

The effective blood substitute besides being able to immediately maximize blood flow (vasodilation) and tissue/organ perfusion (oxygenation), these products should also stimulate erythropoiesis. Since the circulatory retention time of blood substitute is short (half-life of less than 24 hours) and the heme autoxidation rate is high (more than 30% per day), the erythropoietic activity of these products is an essential component in blood loss anemia treatment. The oxidized heme looses its ability to transport oxygen, therefore the stimulation of erythropoiesis becomes an extremely important element of treatment with blood substitute. A speedy replacement of blood loss with the endogenous red blood cells seems to be the most attractive future of blood substitute. In another words, in a treatment of acute anemia the blood substitute should work as a temporary "oxygen" bridge until the body will be able to produce enough red blood cells to maintain proper tissue oxygenation. (Workshop on Criteria for Safety and Efficacy Evaluation of Oxygen Therapeutics as Red Cell Substitutes (1999) NIH, Bethesda, Md.).

Erythropoiesis, an integral part of hemopoiesis, is the development of red blood cells from pluripotent stem cells through several stages of cell division and differentiation. The pluripotent stem cell gives rise to myeloid stem cells (CFU-GEMM) that turn into the burst-forming units erythroid cells (BFU-E), then into the colony forming unit erythroid cells (CFU-E) and pro-erythroblasts. A pro-erythroblast turns into basophilic normoblast and polychromatophilic erythroblast as the cell begins to produce hemoglobin. Then into the orto-chromatic erythroblast when the cytoplasm becomes more eosinophilic. After extruding its nucleus the cells enter circulation as reticulocytes and within a few days become mature red blood cells after loosing their polyribosomes. In normal conditions, the entire erythropoietic process should take no more than 5 days. The life span of mature red blood cells is approximately 90-120 days and requires their continuous replacement (Hillman R S, Finch C A: Red Cell Manual. $7^{th}$ ed., Philadelphia: F. A. Davis, c1996, viii, 190 pp.).

The regulation of erythropoiesis is a complex process controlled by a highly sensitive feedback system based on oxygen tension (concentration) and the cellular redox-state that involves oxygen and redox regulated transcription factors and many growth factors (erythropoietin-EPO, IL-3, IL-9, SCF, GM-CSF) and minerals, particularly iron (Adamson J W (1991) Biotechnology 19:351-361; Sasaki R (2003) Int Med 42(2): 142-149; Lacombe C et al. (1998) Haematologica 83(8):724-732).

While EPO is not the sole growth factor responsible for erythropoiesis, it is the most important regulator of the proliferation of committed progenitors and an anti-apoptotic protector. A principal function of EPO through the EPO receptor (EpoR) is to rescue the committed erythroid progenitors from apoptosis. EPO-dependent upregulation of the antiapoptotic protein Bcl-X(L) allows "default" terminal differentiation of apoptosis-protected, committed erythroblasts, independent of any exogenous signals (Socolovsky et al. (1999) Cell 98(2):181-91; Dolznig et al. (2002) Curr Biol 12(13):1076-1085).

A schematic representation of erythropoietic events and factors involved: CFU-GEMM→(EPO, SCF, IL-9)→BFU-E→(EPO, SCF, GM-CST, IL-3)→CFU-E→(EPO, GM-CSF)→ERYTHROBLAST (EPO)→RETICULOCYTE→RBC Anemia is defined as a pathologic deficiency of oxygen-carrying capacity of blood, resulting in hypoxia. The main causes of anemia are acute blood loss, chronic illnesses secondary to refractory anemia, cancer, intravascular hemolysis, and increase in red blood cell sequestration or decrease of its production. A natural response to hypoxia is an increase in the erythropoietic response (Campbell K. (2004) Nurs Times 100(47):40-43).

Hypoxia simulates the peritubular interstitial cells of the kidney (cortex) to produce EPO. EPO is also synthesized in the liver, and astrocytes in the brain where it protects against neuronal apoptosis and damage during hypoxia. Oxygen-regulated transcription factors; hypoxia inducible factor-1 alpha (HIF-1 alpha) and -1 beta (HIF-1 beta) mediate this process which goes under the control of a single gene on human chromosome 7. HIF-1 that binds specifically to the 3' enhancer of the gene encoding EPO is also a promoter in other genes important in adaptation to hypoxia (Semenza et al. (1992) Mol Cell Biol 12; 5447-5454; Brines et al. (2005) Nat Rev Neurosci 6(6):484-494).

HIF-1, identified by Semenza & Wang, is a heterodimer composed of two basic helix loop-helix/PAS proteins (HIF-1 alpha) and the acryl hydrocarbon nuclear translocator HIF-1 beta. HIF-1 beta is not affected much by oxygen, whereas HIF-1 alpha is present only in the hypoxic condition. In normoxia, the degradation of HIF-1 alpha depends on oxygen mediated hydroxylation of its proline residues by pyrol-4-hydroxylase. Hydroxylation of HIF-1 alpha initiates its rapid degradation by the von Hippel-Lindau tumor suppressor protein that binds to the hydroxylated but not to the non-hydroxylated domain. The von Hippel-Lindau tumor suppressor protein is a part of an ubiquitin ligase linking HIF-1 alpha to the ubiquitination machinery (Wang et al. (1995) J Biol Chem 270; 1230-1237; Wang et al. (1993) J Biol Chem 268; 21513-21518; Kallio et al. (1999) J Biol Chem 274(10):6519-6525).

In the hypoxic condition, however, a lack of oxygen suppresses the degradation of HIF-1 alpha, which rapidly translocates from the cytoplasm to the nucleus and acts as a master regulator of several dozens of oxygen-regulated target genes involved in:

1) oxygen transport: erythropoiesis (EPO); iron transport (transferrin); iron uptake (transferrin receptor), 2) vascular regulation: angiogenesis (VEGF, EG-VEGF, PAI-1); control of vascular tone (iNOS, alpha 1 B-adrenergic receptor, ET-1); vascular remodeling (HO-1), 3) anaerobic energy: glucose uptake (glucose transporter 1); glycolysis regulation (PFKFB3); glycolysis (phosphofructokinase 1, aldolase, GAPDH, phosphoglycerate kinase 1, enolase 1, lactate dehydrogenase A (Wenger R H (2002) FASEB J 16; 1151-1162; Gleadle et al. (1997) Blood 89(2): 503-509; Gleadle et al. (1998) Mol Med Today 4(3):122-129).

HIF-1 alpha can also be stabilized in normoxia. For instance, in oxidative stress the reactive oxygen species (ROS) by changing the cellular redox equilibrium that activates NF-kappa B and induces inflammatory genes (i.e., TNF-alpha, IL-1 beta, IL-6), may stabilize HIF-1 alpha. These inflammatory cytokines, however, can also inhibit HIF-1 alpha binding to the EPO gene while promoting VEGF gene induction, thus suppressing erythropoiesis and accelerating angiogenesis. In cancer patients this phenomena may result in severe anemia and excessive tumor growth, due to effective angiogenesis. Similarly, an other inflammatory mediator TGF-beta, which is also known to stabilize HIF-1 alpha under normoxic conditions, is capable of blocking the differentiation of erythroid progenitor cells while decreasing EPO's erythropoietic activity (Hellwing-Burgel et al. (1999) Am Soc Hematol 94:1561-1567; Linch D C (1989) Schweiz Med Wochenschr 119(39): 1327-1328).

Inflammation is also implicated in the pathogenesis of EPO resistance in patients with end-stage renal disease. TNF-alpha, IL-1 beta and IL-6 are suggested to suppress erythropoiesis in uremia. In animal models and in humans, administration of IL-6 causes a hypoproliferative anemia by direct inhibition upon erythroid progenitor cells (Trey et al. (1995) Crit Rev Oncol Hematol 21:1-8; Yuen et al. (2005) ASAIO J 51(3):236-241).

Other factors known to stabilize HIF-1 alpha under normoxic conditions include NO, PDGF, and oxLDL. The molecular pathways that govern HIF-1 alpha normoxic regulation is mediated by ROS, PI3K, TOR and MAP kinases, particularly ERK 1/2 (Haddad et al. (2000) J Biol Chem 275(28):21130-21139; Haddad et al. (2001) FEBS Lett 505 (2):269-274; Lando et al. (2000) J Biol Chem 275(7):4618-4627; Richard et al. (1999) J Biol Chem 274(46):32631-32637).

The first observation about the possible involvement of free hemoglobin in erythropoietic responses came in 1949 from Amberson, who observed an increase in erythropoiesis indicators (reticulocyte count and hematocrit) in a human after administration of crude hemoglobin solution. This experiment ended tragically with patient death due to the renal failure (Amberson et al. (1949) J Appl Physiol 1:469-489). A clinical trial conducted 30 years later by Savitsky who infused stroma-free hemoglobin solution into normal human volunteers had a similar tragic consequence. All subjects treated with this hemoglobin showed systemic hypertension and renal failure, while one person died (Savitsky et al. (1978) Clin Pharmacol Ther 23:73-80).

These early clinical experiments proved that uncrosslinked hemoglobin is deadly and not suitable for transfusion. At that time the authors have been unable to explain the mechanism of these pathological events. By applying current knowledge, it is reasonable to suggest that the pathological responses seen in Amberson's and Savitsky's clinical trials, particularly, rapid rise in blood pressure, was a result of intrinsic toxicity of hemoglobin. Now, it is obvious that hemoglobin-based blood substitute by scavenging nitric oxide and affecting other vascular tone controlling-mechanisms can produce severe rise in blood pressure which is associated with decreased cardiac output and increased total vascular peripheral resistance (Simoni J. (2005) In: Artificial Oxygen Carrier. Its Front Line. K. Kobayashi et al. (Eds.). Springer-Verlag, Tokyo, 2005 pp. 75-126).

Hemoglobin is a pressor agent and the presently used chemical or recombinant modification techniques did not correct this problem. All tested blood substitute products, including HEMASSIST™, OPTRO™-rHb1.1, POLYHEME®, HEMOPURE® and HEMOLINK™ caused vascular constriction—a side effect that has been the main nemesis of blood substitute developers. The observed increase in blood pressure after injection of these blood substitute is caused by an increase in peripheral vascular resistance resulting from vasoconstriction (Winslow R M (1994) Transf Clin Biol 1(1); 9-14; Hess et al. (1994) Artif Cells Blood Substit Immobil Biotechnol 22(3):361-372; Kasper et al. (1996) Cardiovasc Anesth 83(5):921-927; Kasper et al. (1998) Anesth Anal 87(2):284-291; Winslow R M (2003) J Intern Med 253: 508-517). In was also reported that some of the products have a tendency to shut down capillary flow, which may decrease the tissue/organ perfusion rate and produce hypoxia (Cheung et al. (2001) Anesth Anal 93(4):832-838).

Since the hypoxic environment stabilizes HIF-1 alpha, it is theoretically possible that blood substitute that promote vasoconstriction and produce hypoxia might induce HIF-1 alpha regulated genes. This mechanism, however, is in contradiction to the main role for blood substitute, which is delivery of a sufficient amount of oxygen to the tissues gasping for air. The proper delivery of oxygen to ischemic organs is a principal requirement in the regulatory approval of hemoglobin solutions as blood substitute. Therefore such an "erythropoietic effect" should be considered pathological. To be considered non-toxic and efficacious, blood substitute products should maximize blood flow and tissue perfusion and therefore, oxygenation (Workshop on Criteria for Safety and Efficacy Evaluation of Oxygen Therapeutics as Red Cell Substitutes (1999) NIH, Bethesda, Md.; Guidance for Industry. Criteria for Safety and Efficacy Evaluation of Oxygen Therapeutics as Red Cell Substitutes (2004) U.S. Department of Health and Human Services, Food and Drug Administration, Center for Biologies Evaluation and Research, Rockville, Md.).

It is also theoretically possible, that such blood substitute, when used in larger doses, can trigger inflammatory reactions which might inhibit their initial, hypoxic-driven erythropoietic response.

In the 1990's, Simoni et al. discovered that hemoglobin is a potent inducer of the redox regulated transcription factor NF-kappa B that is involved in the regulation of genes involved in inflammation. He found that the activation of the endothelial NF-kappa B might be dependent on hemoglobin's pro-oxidant potential and the extent of hemoglobin-mediated cellular oxidative stress that shifts GSH/GSSG into an oxidative equilibrium. In this study, the glutaraldehyde polymerized bovine hemoglobin appeared to be a more potent inducer of NF-kappa B than unmodified hemoglobin. Simoni et al. linked this effect with the fact that glutaraldehyde polymerized hemoglobin produced the highest endothelial lipid peroxidation and the largest depletion of intracellular GSH. Based on these studies, Simoni et al. suggested that the activation of NF-kappa B could be considered as a "bridge" between hemoglobin-induced oxidative stress and hemoglobin-mediated inflammatory responses. Besides, his discovery established the foundation for seeing hemoglobin as a signaling molecule (Simoni et al. (1997) Artif Cells Blood Substit Immobil Biotechnol 25(1-2): 193-210; Simoni et al. (1997) Artif Cells Blood Substit Immobil Biotechnol 25(1-2):211-225; Simoni et al. (1998) ASAIO J 44(5):M356-367; Simoni et al. (1994) Artif Cells Blood Substit Immobil Biotechnol 22(3):525-534; Simoni et al. (2000) ASAIO J 46(6):679-692; Simoni et al. (1994) Artif Cells Blood Substit Immobil Biotechnol 22(3):777-787; Pahl H L (1999) Oncogene 18:6853-6866; Gilmore T D (2005)).

Subsequent research by Simoni, established evidence that hemoglobin solutions which trigger NF-kappa B may suppress HIF-1 alpha regulated genes, particularly EPO (Simoni et al (2003) Artificial Blood 11(1):69; Simoni et al. (2003) ASAIO J 49(2):181; Simoni J. (2005) In: Artificial Oxygen Carrier. Its Front Line. K. Kobayashi et al. (Eds.). Springer-Verlag, Tokyo, 2005 pp. 75-126).

It was also reported that high activity of the NF-kappa B pathway in early erythroid progenitors is involved in the suppression of erythroid-specific genes (Liu et al. (2003) J Biol Chem 278(21):19534-19540).

Inflammation is generally accepted to contribute to the pathogenesis of EPO resistance, particularly in anemia and cancer (Yuen et al. (2005) ASAIO J 51 (3):236-241; Hellwig-Burgel et al. (1999) 94(5):1561-1567).

Therefore, it is theoretically possible that blood substitute, which change the cellular redox state, might trigger NF-kappa B regulated genes (i.e., cytokines) and stabilize HIF-1 alpha even in the normoxic environment. However, in such a condition, effective binding of HIF-1 alpha to the EPO gene is inhibited by the inflammatory cytokines. Since hemoglobin is linked to the production of inflammatory cytokines, and the inflammatory cytokines are potent anti-erythropoietic agents, it is reasonable to suggest that the blood substitute with high pro-inflammatory potential could inhibit the erythropoietic responses.

In fact, it was reported that some of the currently tested blood substitute mediate not only vasoconstrictive events, but they are also capable to induce inflammatory reactions. Those responses were more evident during a dose escalation study (late phases of clinical trials) and have been observed with Baxter's HEMASSIST™, Biopure's HEMOPURE®, Somatogen's rHb1.1-OPTRO™ and Northfield's POLY-HEME®. The vasoconstriction and ischemic/inflammatory responses were cited as the main reason for redirecting, halting, or discontinuing the clinical development of these blood substitute (Simoni J. (2005) In: Artificial Oxygen Carrier. Its Front Line. K. Kobayashi et al. (Eds.). Springer-Verlag, Tokyo, 2005 pp. 75-126).

Another scientific rationale against the possible erythropoietic activity of the currently tested blood substitute is the fact that hemoglobin has a natural pro-apoptotic potential. This observation is very important since the principal function of EPO as a pro-erythropoietic agent is to protect committed erythroblasts from apoptosis, thus allowing erythropoiesis to happen (Socolovsky et al. (1999) Cell 98(2): 181-91; Dolznig et al. (2002) Curre Biol 12(13): 1076-1085).

It was reported that unmodified hemoglobin has pro-apoptotic potential toward human endothelial cells and that caspase-8 and -9 controls this effect, which can be accelerated by depletion of intracellular GSH (Meguro et al. (2001) J Neurochem 77(4): 1128-1135; Simoni et al. (2002) ASAIO J 48(2): 193). A diaspirin modified hemoglobin (HEMASSIS™) and its glutaraldehyde-polymerized version also induces morphological changes, G2/M arrest, and DNA fragmentation, indicative of apoptotic cell death (Goldman et al. (1998) Am J Physiol 275(3 Pt2):H1046-53); D'Agnillo et al. (2001) Blood 98(12):3315-3323). Oxyglobin, a veterinary version of HEMOPURE® (Biopure), used in ex vivo heart perfusion model, was found to produce apoptotic endothelial cells death (TUNEL assay) that was associated with a significant increase in coronary artery resistance (Mohara et al. (2005) ASAIO J 51(3):288-295).

It became evident that any agent with pro-apoptotic potential that has direct contact with the bone marrow cells has anti-erythropoietic activity. Such an agent will compete with the anti-apoptotic effects of EPO, making erythropoiesis impossible. In fact, hemoglobin based blood substitute are partially cleared up by the bone marrow cells, therefore, they are in a direct contact with erythroblasts (Shum et al. (1996) Artif Cells Blood Substit Immobil Biotechnol 24(6):655-683).

Realizing that hemoglobin has pro-apoptotic potential and can have direct contact with the bone marrow, it is reasonable to suggest that any blood substitute product with pro-apoptotic activity when given in a relatively high concentration will inhibit erythropoiesis.

In scientific and patent literature, there is limited information about the erythropoietic potency of hemoglobin-based blood substitute. In 1997, Rosenthal et al. (U.S. Pat. No. 5,631,219) claimed the method for stimulation of hemopoiesis in a mammal with the recombinant hemoglobin (rHb1.1) through enhancing growth or differentiation of progenitor stem cells including erythroid progenitor cells. U.S. Pat. Nos. 5,028,588, 5,563,254 and 5,661,124 to Hoffman et al. protects the recombinant hemoglobin rHb1.1 (trade name OPTRO™).

In U.S. Pat. No. 5,631,219, rHb1.1 in a dose of either 0.5 or 1.0 mg/kg body weight, given intravenously three times per week to mice, resulted in a increased BFU-E that are early precursors of red blood cells in the bone marrow. In U.S. Pat. No. 5,631,219, Rosenthal et al. reported an increase in hematocrit following the treatment of normal mice (BDF-1) with rHb1.1. To evaluate whether rHb1.1 acted at a level other than the committed erythroid precursor, Rosenthal evaluated the influence of rHb1.1 on very early, uncommitted progenitor cells, the colony forming unit-spleen (CFU-S).

According to U.S. Pat. No. 5,631,219, Rosenthal found that rHb1.1 in a concentration of 0.5 mg/kg body weight increases the number of CFU-S. In U.S. Pat. No. 5,631,219, the lower dose level of 0.5 mg of hemoglobin/kg body weight appears to work better than the higher doses of rHb1.1 (5 and 10 mg/kg), suggesting a maximum effect at unexpectedly low doses.

Without providing any theoretical explanation, Rosenthal et al. concluded that rHb1.1 at low doses (0.5 mg/kg body weight) works either directly on progenitor cells or indirectly to enhance hematopoiesis and acts as an erythropoietic factor.

The concentration of rHb1.1 used by Rosenthal et al. (0.5-10 mg/kg body weight) was clinically irrelevant in respect to oxygen transport, therefore the treatment of acute blood loss. To be therapeutically effective, hemoglobin-based blood substitute should be transfused in grams, but not milligrams. Therefore, the U.S. Pat. No. 5,631,219 could not apply to the treatment of acute blood loss anemia.

Furthermore, the patented claims in U.S. Pat. No. 5,631,219 are in disagreement with the examples provided. Rosenthal has claimed the therapeutically effective level of hemoglobin to be between 0.001 and 10,000 mg/kg body weight. These claims are not supported by Rosenthal's examples that showed that rHb1.1 in a concentration of only 0.5 mg/kg body weight had hemopoietic effect. Perhaps, Rosenthal was influenced by our published paper in which chemically modified bovine hemoglobin solution in a dose of approximately 1.75 g (1,750 mg)/kg body weight showed an effective erythropoietic response in man. U.S. Pat. No. 5,631,219 relies on this paper (Feola et al. (1992) Surg Gynecol Obstet 174(5):379-386).

In 1997, Moqattash et al. compared the ability of infused rHb1.1 and EPO to rescue the hematopoietic activity from the suppressive effects of AZT in normal and AIDS mice. The result showed that higher concentrations of rHb1.1 used (10-15 mg/kg body weight) did not result in a more significant increase in most blood indices. Moreover, the combination treatment, 5-mg rHb1.1/kg body weights plus 2 U EPO/mouse/day, was showed to work better than 5-mg/kg-body weight of rHb1.1 alone (Moqattash et al. (1997) Acta Haematol 98(2):76-82).

Two years later, Lutton et al. successfully challenged Rosenthal's work. By analyzing the hematopoietic effect of clinically relevant doses of cross-linked and non-cross-linked hemoglobin in rabbits, he concluded that both hemoglobin solutions at high concentrations did not produce a significant variation in the generation of BFU-E and CFU-S, thus, they do not represent any hemopoietic activity (Lutton et al. (1999) Pharmacology 58:319-324).

The recombinant (i.e., rHb1.1), cross-linked tetrameric (i.e., HEMASSIST™), and polymerized (i.e., HEMOPURE®, POLYHEME®) hemoglobins have been extensively tested in various preclinical and clinical studies. All tested hemoglobin solutions showed to be toxic (Workshop on Criteria for Safety and Efficacy Evaluation of Oxygen Therapeutics as Red Cell Substitutes (1999) NIH, Bethesda, Md.).

The human clinical trial with rHb1.1 in which 48 healthy male volunteers were randomly assigned to receive 15-320 mg/kg body weight of 5% rHb1.1 was associated with serious side effects, such as gastrointestinal upset, fever, chills, headache, and backache (Viele et al. (1997) Anesthesiology 86(4): 848-858). In another clinical study with the patients undergoing surgery and receiving 67-365 mg/kg body weight of rHb1.1, no serious adverse events occurred. However, patients suffered from hypertension, inflammatory symptoms and elevated pancreatic enzymes. In these clinical trials, the erythropoietic effects of rHb1.1 were also not reported (Hayes et al. (2001 Cardiothorac Vasc Anesth 15(5):593-602).

Highly unsatisfactory clinical experience with rHb1.1 had ended the commercial development of this recombinant blood substitute product. In the late 90's, Somatogen/Baxter focused on a novel second-generation recombinant product (rHb2.0; U.S. Pat. No. 6,022,849 to Olson et al.) to replace the clinically unsuccessful rHb1.1. The new product was designed to have a lower rate of reaction with nitric oxide. However, after 2 years of pre-clinical testing, the commercial development of rHb2.0 was also discontinued.

Clinical experience with rHb1.1 can help understand why in U.S. Pat. No. 5,631,219 the lower dose level (0.5 mg of hemoglobin/kg body weight) appeared to work better than the higher doses (5 and 10 mg/kg). Perhaps, strong pro-inflammatory and pro-apoptotic potential of the higher doses of rHb.1.1 suppresses the induction of the EPO gene, making erythropoiesis impossible. Therefore, it is reasonable to suggest that rHb1.1 in higher concentrations than a few mg/kg body weight would produce the inhibition of erythropoiesis, while promoting the production of pro-inflammatory phagocytes as a part of the hemopoietic-inflammatory event.

Other hemoglobin based blood substitute products were also unsuccessful in late phases of clinical trials.

Phase III studies with HEMASSIST™ ended tragically. The patients treated with HEMASSIST™ had significantly higher mortality rates than those of the control group. In June 1998, upon recommendation of the FDA, the development program of HEMASSIST™ was suspended due to safety concerns. In HEMASSIST™ clinical trials, the erythropoietic or hemopoietic effect was not reported (Sloan et al. (1999) JAMA 282:1857-1864).

The clinical development of HEMOPURE® (U.S. Pat. Nos. 5,084,558, 5,296,465 and 5,753,616 to Rausch et al.; U.S. Pat. No. 5,895,810 to Light et al.) was put on clinical hold due to "safety concerns." The strong vasoconstrictive, pro-oxidant, pro-inflammatory and pro-apoptotic potential of this product could inevitably limit its practicability as a blood substitute (Kasper et al. (1996) Cardiovasc Anesth 83(5):921-927; Kasper et al. (1998) Anesth Anal 87(2):284-291).

The erythropoietic effect of HEMOPURE® alone was never substantiated (Gawryl M S (2003) Artif Blood 11(1): 46). However, HEMOPURE® (plus EPO) was used experimentally in the treatment of severe anemia after gastrointestinal hemorrhage in a Jehovah's Witness. A 50-yr-old man with initial hemoglobin of 3.5 g/dL was injected with HEMOPURE® (7 units) and with a high-dose of recombinant EPO (500 U/kg/day). Hemoglobin levels were initially maintained and then slowly increased to a maximum of 7.6 g/dL on day 24 of rEPO therapy. This case demonstrates that HEMOPURE® (with a half life less than 24 hours) can serve as initial therapy while awaiting the maximal effect of recombinant EPO on bone marrow red blood cell production. This clinical study showed that HEMOPURE® alone does not have erythropoietic potential (Gannon et al. (2002) Crit Care Med 30(8):1893-1895).

In 2002, POLYHEME® (U.S. Pat. Nos. 4,826,811, 5,194,590, 5,464,814, 6,133,425, 6,323,320 and 6,914,127 to Sehgal et al.) failed to receive U.S. regulatory approval for use in elective surgery patients. Now, POLYHEME® is clinically tested on a compassionate use basis to treat severe hemorrhage of auto accident victims.

In the past POLYHEME® was used to treat a critically anemic woman who suffered from persistent colonic bleeding and hemoglobin of 2.9 g/dL. In this clinical study, POLYHEME® was used together with high dose of recombinant EPO, which was needed to stimulate erythropoietic responses. Therefore, it is highly probable that POLY- HEME®, similarly to HEMOPURE®, does not alone have any erythropoietic activity (Allison et al. (2004) Southern Med J 97(12): 1257-1258).

The clinical development of HEMOLINK™ (U.S. Pat. No. 4,857,636 to Hsia) was halted because of increased myocardial infarction (inflammation-based) rates in humans. HEMOLINK™ was shown to be less stable in respect to autoxidation, oxidative modification, and the integrity of the heme group compared to native hemoglobin. HEMOLINK™ that represents high vasoconstrictive, pro-oxidative and pro-inflammatory properties was never characterized as a product that stimulates erythropoiesis alone (Alayash Al (2004) Nature 3:152-159; Riess J G (2001) Chem Rev 101(9):2797-2919).

In the past, similarly to other blood substitute products (HEMOPURE®, POLYHEME®), HEMOLINK™ was tested in compassionate treatment of a 53-yr-old female Jehovah's Witness with severe anemia and hemoglobin of 3.2 g/dL. Also in this trial, HEMOLINK™ was administrated along with a high dose of recombinant EPO and ferrous sulfate. After 14 days, the patient's hemoglobin level increased to only 6.5 g/dL with a hematocrit of 23%. This trial provided more evidence that toxic hemoglobin based blood substitute could not alone stimulate erythropoietic events (Lanzinger et al. (2005) Can J Anaesth 52(4):369-373).

The basic research on erythropoietic activity of hemoglobin is also very limited. Recently, it was reported that hemoglobin under hypoxic conditions increased the expression of HIF-1 alpha. Using a bovine aortic endothelial cell model and the Western Blot method for the detection of HIF-1 alpha it was suggested that the higher expression of HIF-1 alpha is connected with the loss of ferrous- and accumulation of ferric-Hb (oxidation of heme), in both unmodified hemoglobin solutions. In this study, the authors used the diaspirin cross-linked hemoglobin, similar to that of HEMASSIST™ (Yeh et al. (2004) Antioxid Redox Signal 6:944-953).

This experiment besides providing more molecular details for an earlier suggestion that prolonged exposure of endothelial cells to ferric-(oxidized) but not ferrous-(oxygenated) hemoglobin renders these cells remarkably resistant to the secondary oxidant challenge via increased production of HO-1 and ferritin, also suggest that the phenomenon is now known to be HIF-1 alpha regulated (Balla et al. (1995) Am J Physiol 268(2 Pt 1):L321-327).

Because efficacious hemoglobin-based oxygen carriers must be able to counteract the hypoxic conditions associated with blood loss anemia, the above findings may only apply to those products that aggravate hypoxia, thus inducing HIF-1 alpha. In fact, the blood substitute products under current clinical development possessed well-documented vasoconstrictive potential and high autoxidation rate. In Yeh's work, however, no connection between hemoglobin and erythropoiesis has been made.

An evident lack of erythropoietic activity of blood substitute under current development can be summarized by the statement of Dr. Harvey G. Klein from the Department of Transfusion Medicine, Warren G. Magnuson Clinical Center, National Institute of Health, Bethesda, Md. In his 2005 review paper entitled: "Blood substitutes: how close to a solution?" he stated that: " . . . hemoglobin-derived red cell substitutes from human, bovine and recombinant sources in phase III trials all have a half-life measured in hours and are unlikely to replace transfusions or drugs that stimulate erythropoiesis for chronic anemia, but they may play role: (1) as a bridge to transfusion when no compatible blood is immediately available, (2) as an adjunct to the autologous hemodilution management of surgery, or even (3) in radiation therapy or the management of cancer . . . " (Klein H G (2005) Dev Biol (Basel) 120:45-52).

The above analysis illustrates that the ideal blood substitute was not yet developed. The perfect blood substitute should sustain the patient until hemorrhage will be controlled. Since acellular blood substitute have short circulatory half-lives they should have an ability to stimulate erythropoiesis to compensate the blood loss. To sustain the patient, blood substitute should maximize blood flow and tissue perfusion and therefore, oxygenation. To stimulate erythropoiesis, blood substitute should stabilize HIF-1 alpha under hypoxic and normoxic conditions and by controlling the pro-oxidative and pro-inflammatory reactions should facilitate HIF-1 alpha binding to the EPO-gene. The blood substitute should also not be involved in any pro-apoptotic activity, since a principal function of EPO is to rescue committed erythroid progenitors from apoptosis. These events are necessary to initiate an effective erythropoiesis that in turn will momentarily compensate lost blood with endogenous red blood cells.

A proper delivery of oxygen to ischemic organs is the principal requirement in the regulatory approval of hemoglobin solutions as blood substitute. Therefore, blood substitute that induce vasoconstriction and possess strong pro-oxidative, pro-inflammatory and pro-apoptotic potential could be harmful to the patient and are clinically unacceptable.

The products presently under clinical trial represent the first generation of blood substitute, with effort now directed towards a "new generation" of blood substitute which addresses all of the hemoglobin intrinsic toxicity problems. It is believed that the second-generation products could be used for all clinical indication, including treatment of acute blood loss anemia and trauma.

Since the currently tested blood substitute lack erythropoietic activity, there still exists a need for an improved oxygen carrying solution, which will have the ability to maximize tissue perfusion and oxygenation and stimulate erythropoiesis, thus, replace lost blood with endogenous red blood cells. The stimulation of erythropoiesis by such blood substitute should occur in hypoxic and normoxic conditions. In the case of life-threatening anemia, such blood substitute should serve as initial therapy to maintain tissue oxygenation and secondary therapy to normalize the hematocrit through stimulation of patients' erythropoietic responses through stabilization of HIF-1 alpha and EPO production. This therapy should eliminate the need for an expensive recombinant EPO medication.

In the patent literature there are some indications that stabilization of HIF-1 alpha could provide therapeutic benefits in the treatment of hypoxia related tissue injury. U.S. Pat. No. 6,562,799 to Semenza provides a method for treating a hypoxia- or ischemia-related tissue damage by administering to the subject a therapeutically effective amount of a stable HIF-1 alpha protein. U.S. Pat. No. 6,432,927 to Gregory, et al. provides a method for reducing ischemic tissue damage with the DNA binding domain of a hypoxia inducible factor protein capable of transcriptional activation. Kaelin et al. in U.S. Pat. No. 6,849,718 provides pharmaceutical compositions containing HIF-1 alpha muteins and method of using those compositions to treat hypoxia and ischemic related tissue damage. U.S. Pat. No. 6,838,430 to Arbeit provides the use of stable HIF-1 alpha variants to accelerate wound healing.

These patented methods, however, do not concern the use of hemoglobin based blood substitute in promoting HIF-1 alpha dependent EPO induction, therefore erythropoiesis.

Optimizing oxygen delivery to ischemic tissue and organs and effective stimulation of erythropoietic responses are the most important factors in the regulatory approval of these agents as blood substitute. The blood substitutes of the present invention address the problems discussed above.

2.2. Acute Blood Loss Therapies

There is currently no regulatory approved blood substitute in the United States. As such, blood transfusion is the only reliable means of rapidly restoring blood volume in a subject with acute blood loss. However, there are a number of risks associated with blood transfusion. First, donor blood needs to be tested to determine its suitability for transfusion and compatibility to the recipient. Compatibility testing usually involves (1) ABO typing of donor and recipient blood to prevent transfusion of incompatible red blood cells (RBCs); and (2) Rh typing to determine whether the Rh factor Rh0(D) is present (Rh-positive) or absent (Rh-negative) on the RBCs. The donated blood also needs to be screened to identify unexpected anti-RBC antibodies that can cause hemolytic disease or serious transfusion reaction using for example, direct antiglobulin testing (the direct Coombs' test) and indirect antiglobulin testing (the direct Coombs' test).

Assuming the donor blood is a match for the recipient, many complications can still result due to blood transfusion. For example, hemolysis of donor or recipient RBCs (usually the former) during or after transfusion can result from ABO/Rh incompatibility, incompatible plasma, hemolyzed or fragile RBCs (e.g., by overwarming stored blood or contact with inappropriate IV solutions), or injections of nonisotonic solutions. The reaction is most severe when incompatible donor RBCs are hemolyzed by antibody in the recipient's plasma and can cause breathing difficulty, fever and chills, facial flushing, severe pain (especially in the lumber area), as well as shock that lead to a drop in blood pressure, nausea and vomiting. Allergic reactions to an unknown component in donor blood are also common, usually due to allergens in donor plasma or, less often, to antibodies from an allergic donor. These reactions are usually mild, with urticaria, edema, occasional dizziness, and headache during or immediately after the transfusion, although anaphylaxis may occur in some rare instances. Another complication, though less frequent, is transfusion-related acute lung injury that is caused by anti-white blood cell (WBCs) antibodies in donor plasma that agglutinate and degranulate recipient WBCs within the lungs. Transfusion of large amounts of air into a vein can also cause foaming of blood in the heart with consequent inefficient pumping, leading to heart failure. Graft-vs.-host disease, which can be caused by even small numbers of viable lymphocytes in transfused blood or blood components, can also result from a blood transfusion. There is also the concern of bacterial contamination which may occur due to inadequate aseptic technique during collection or by transient asymptomatic donor. Finally, and most importantly, recipients of blood transfusion will always have the risk of viral disease transmission, including, but not limited to, hepatitis, HIV, cytomegalovirus (CMV), and human T-cell lymphotropic virus type I (HTLV-I) infection.

3. SUMMARY OF THE INVENTION

The present invention relates to methods using certain blood substitutes for treating or preventing acute blood loss anemia, namely anemia caused by (i) acute blood loss due to an illness, (ii) acute blood loss that occurs during surgery, or (iii) acute blood loss from trauma, in subjects in need thereof. The methods of the invention involve the use of a blood substitute that both restores blood volume and counters hypoxia, and induces erythropoiesis under normoxic conditions. Blood transfusion, which is currently the only reliable means of rapidly restoring blood loss in a subject, is effective at restoring blood volume and countering hypoxia. However, it is not desirable to use blood transfusions during emergency caused by acute blood loss because there is no time to test for compatibility between the donor and recipient blood, and there is always the risk of triggering many complications associated with immunological components that are present in donor blood (e.g., hemolysis of RBCs, allergic reactions, transfusion-related acute lung injury, graft-vs.-host disease, bacterial contamination, viral disease transmission, etc.). Moreover, blood transfusions, which temporarily restore normoxic conditions, compromise the body's ability to replenish its own red blood cells. In particular, increased production of erythropoietin in the body, which is responsible for erythropoiesis, is induced by hypoxic conditions. Thus, blood transfusions, while a "quick fix" for hypoxia, ultimately slow down erythropoiesis, and therefore, the body's ability to replenish the circulation with endogenous red blood cells. The blood substitutes currently being tested for human use are problematic for a similar reason. In particular, the circulatory retention time of many blood substitutes is short (half-life of less than 24 hours) and the heme autoxidation rate is high (more than 30% per day), and thus, do not possess the necessary erythropoietic activity to replenish the body's circulation with endogenous red blood cells. The present invention alleviates this problem because the blood substitutes used in the methods of the present invention are capable of inducing erythropoiesis even under normoxic conditions.

In certain embodiments, the blood loss is associated with an illness such as a hemorrhagic disease, an ulcer, or a ruptured vessel or aneurysm. In certain other embodiments, the blood loss occurred during a surgery such as an elective surgery (e.g., orthopedic surgery). In certain other embodiments, the blood loss is from trauma such as a burn injury, a gunshot wound or a stab wound. In certain embodiments, the blood loss is severe such that the subject has greater than 33% blood loss. In certain other embodiments, the blood loss is moderate such that the subject has from about 20% to 33% blood loss. In certain other embodiments, the blood loss is mild such that the subject has less than 20% blood loss. Preferably, the subject is a human. Human subjects that have less than 7 g/dL hemoglobin may advantageously be treated using the methods of the invention.

The methods of the present invention comprise administering to subjects in need thereof a blood substitute in an amount effective to elevate blood volume and counter hypoxia associated with the acute blood loss. The blood substitutes useful for the methods of the present invention are capable of (1) inducing expression of erythropoietin as tested in a cell culture under normoxic conditions; and/or (2) inducing erythropoiesis under normoxic conditions as measured by (a) a decrease in the doubling time of the subject's hematocrit or hemoglobin, or (b) an increase in the subject's circulating erythropoietin level. Optionally, the blood substitutes can also be shown to stabilize HIF-1 alpha expression as tested in a cell culture, and/or down regulate NF-kappa B expression as tested in a cell culture.

Any blood substitutes which exhibit these characteristics can be used in the methods of the present invention. For example, the blood substitute can be a cross-linked hemoglobin blood substitute, or more specifically, a cross-linked hemoglobin that comprises a hemoglobin that is cross-linked intramolecularly with periodate-oxidized ATP, cross-linked intermolecularly with periodate-oxidized adenosine, and conjugated with reduced glutathione. In preferred embodiments, the cross-linked hemoglobins used in the methods of the present invention comprise hemoglobin and periodate-oxidized ATP at a molar ratio of 1:1 to 1:3; hemoglobin and periodate-oxidized adenosine at a molar ratio of 1:1 to 1:10; and/or hemoglobin and reduced glutathione are at a molar ratio of 1:1 to 1:20. The trademark for this product is HEMO-TECH™, which is a cross-linked hemoglobin that comprises pure bovine Hb cross-linked with o-adenosine 5'-triphosphate (o-ATP), o-adenosine and reduced glutathione (GSH). More details regarding cross-linked hemoglobins can be found in U.S. Pat. No. 5,439,882 to Feola et al., which is incorporated by reference herein in its entirety.

The present invention also relates to novel pharmaceutical compositions comprising certain concentrations or volumes of blood substitutes that can be used in the methods of the invention or for other therapies. For example, such novel compositions can comprise (1) a therapeutically effective amount of (a) from 7 g to less than 122.5 g, or (b) from greater than 122.5 g to 700 g, or (2) a therapeutically effective volume of less than 0.6 liter of a cross-linked hemoglobin blood substitute in a pharmaceutically acceptable carrier, wherein the cross-linked hemoglobin blood substitute, when tested in a cell culture under normoxic conditions, induces expression of erythropoietin.

Other novel pharmaceutical compositions include (1) a therapeutically effective amount of (a) from 7 g to less than 122.5 g, or (b) from greater than 122.5 g to 700 g, or (2) a therapeutically effective volume of less than 0.6 liter of a cross-linked hemoglobin in a pharmaceutically acceptable carrier, wherein the cross-linked hemoglobin is a hemoglobin that is cross-linked intramolecularly with periodate-oxidized ATP, cross-linked intermolecularly with periodate-oxidized adenosine, and conjugated with reduced glutathione.

In certain embodiments, the cross-linked hemoglobins used in the pharmaceutical compositions of the present invention is dissolved in a non-electrolytic aqueous solution. The pharmaceutical compositions can further comprises mannitol and/or electrolytes.

The novel pharmaceutical compositions of the invention can be used in the methods of the invention as well as any other methods (e.g., treating chronic blood loss anemia or anemia caused by long-term blood loss).

The methods of the present invention are illustrated using a cross-linked hemoglobin for acute blood loss treatment in animal subjects.

3.1. Definitions

As used herein, the term "about" is intended to encompass standard experimental error (e.g., standard deviation). More information regarding the definition, calculation, and interpretation of the standard deviation can be found in statistics textbook such as, but not limited to, Statistics, W. W. Norton & Company; 3rd edition (Sep. 1, 1997); and The Basic Principles of Statistics, W.H. Freeman & Company; 3rd Bk&Cdr edition (Jun. 1, 2003).

As used herein, the terms "an effective amount" and "an effective volume" mean an amount and volume, respectively, sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the one or more blood substitutes and/or pharmaceutical compositions of the invention.

As used herein, the terms "hypoxic" and "hypoxia" refer to a state of reduced levels of oxygen. Hypoxia can be caused by the reduction in partial pressure of oxygen, inadequate oxygen transport, and/or the inability of the tissues to use oxygen, and can cause an impairment of body function. A hypoxic condition (1.5% $O_2$, 93.5% $N_2$, and 5% $CO_2$) can be achieved, for example, in a humidified variable aerobic workstation.

As used herein, the term "illness" is used interchangeable with the term "disease." An illness that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract).

As used herein, the terms "normoxic" and "normoxia" refer to a state of normal levels of oxygen. Typically, a normoxic condition refers to a situation in which the partial pressure of oxygen in the inspired gas is equal to that of air at sea level, about 150 mm Hg. Normoxic condition is 95% air and 5% $CO_2$.

As used herein, the terms "prevent," "preventing" and "prevention of" (or grammatically equivalent terms) with respect to acute blood loss refer to delaying or preventing acute blood loss or the symptoms or histopathology associated with acute blood loss.

As used herein, the terms "a prophylactically effective amount" and "a prophylactically effective volume" refer to that amount or volume, respectively, sufficient to delay or prevent a subject from having acute blood loss. For example, the prophylactically effective amount or prophylactically effective volume can refer to an amount or volume of a blood substitute or pharmaceutical composition of the present invention sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the blood substitute or pharmaceutical composition. The prophylactically effective amount or prophylactically effective volume may also refer to an amount or volume of the blood substitutes or pharmaceutical compositions of the present invention that provides a prophylactic benefit in the treatment or management of the symptoms or histopathology associated with acute blood loss. Further, the prophylactically effective amount or prophylactically effective volume with respect to a blood substitute or pharmaceutical composition of the present invention means that amount or volume of the blood substitute or pharmaceutical composition alone, or in combination with other therapies, that provides a prophylactic benefit in the treatment, management, or amelioration of acute blood loss or the symptoms or histopathology associated with acute blood loss.

As used herein, the terms "subject" and "patient" are used interchangeably. The subject can be an animal. In particular, the subject can be a mammal such as a non-primate (e.g., a cow, pig, horse, cat, dog, rat, and mouse) or a primate (e.g., a monkey, such as a cynomolgous monkey, chimpanzee, and a human).

As used herein, the term "surgery" is used interchangeable with the term "operation." A surgery that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract).

As used herein, the terms "a therapeutically effective amount" and "a therapeutically effective volume" refer to that amount and volume, respectively, sufficient to provide some improvement or benefit to a subject with acute blood loss. For example, the therapeutically effective amount or therapeutically effective volume can refer to an amount or volume of a blood substitute or pharmaceutical composition of the present invention sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the blood substitute or pharmaceutical composition. The therapeutically effective amount or therapeutically effective volume may also refer to an amount or volume of the blood substitutes or pharmaceutical compositions of the present invention that provides a therapeutic benefit in the treatment or management of the symptoms or histopathology associated with acute blood loss. Further, the therapeutically effective amount or therapeutically effective volume with respect to a blood substitute or pharmaceutical composition of the present invention means that amount or volume of the blood substitute or pharmaceutical composition alone, or in combination with other therapies, that provides a therapeutic benefit in the treatment, management, or amelioration of acute blood loss or the symptoms or histopathology associated with acute blood loss.

As used herein, the term "trauma" is used interchangeable with the term "injury." A trauma that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract).

As used herein, the terms "treat," "treating" and "treatment of" (or grammatically equivalent terms) with respect to acute blood loss refer to reducing or eliminating acute blood loss or the symptoms or histopathology associated with acute blood loss.

4. BRIEF DESCRIPTION OF THE DRAWINGS

FIG. 6 shows the effect of hemoglobin-ATP-adenosine-GSH-based blood substitute and unmodified hemoglobin solution in concentrations of 0.1, 1.0 and 1.75 g per dL on (A) HIF-1 alpha stability and (B) EPO production by human astrocytes under hypoxic and normoxic conditions.

5. DETAILED DESCRIPTION OF THE INVENTION

Figure 1:
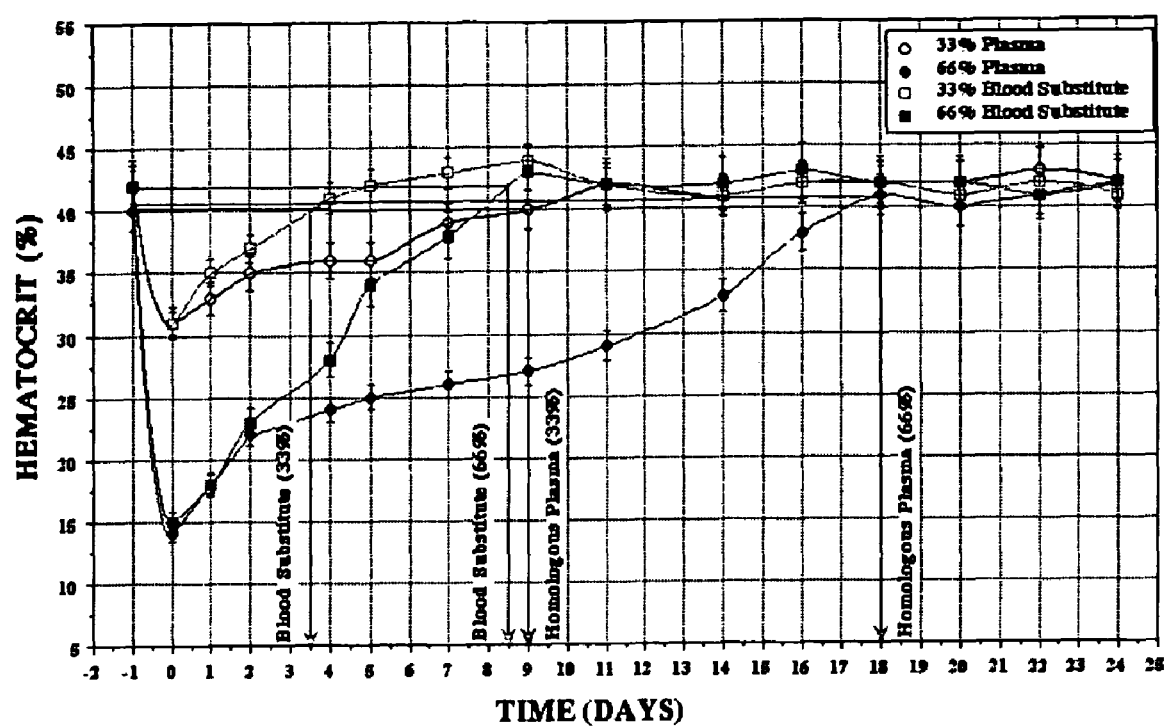
FIG. 1 shows the hematocrit (in percent) of Coebus monkeys suffering from 33 and 66% of the total blood loss treated with hemoglobin-ATP-adenosine-GSH-based blood substitute and homologous plasma.

The present invention relates to novel methods for treating or preventing acute blood loss, preferably, acute blood loss anemia, or more preferably, anemia caused by (i) acute blood loss due to an illness, (ii) acute blood loss that occurs during surgery, or (iii) acute blood loss from trauma. The methods of the present invention comprise administering to subjects in need thereof a blood substitute in an amount effective to elevate blood volume and counter hypoxia associated with the acute blood loss, which blood substitute induces erythropoiesis under normoxic conditions. More particularly, the blood substitutes useful for the methods of the present invention are capable of (1) inducing expression of erythropoietin as tested in a cell culture under normoxic conditions, and/or (2) inducing erythropoiesis under normoxic conditions as measured by (a) a decrease in the doubling time of the subject's hematocrit or hemoglobin, or (b) an increase in the subject's circulating erythropoietin level.

The present invention also relates to pharmaceutical compositions comprising a therapeutically or prophylactically effective amount or volume of a cross-linked hemoglobin blood substitute in a pharmaceutically acceptable carrier, wherein the cross-linked hemoglobin blood substitute, when tested in a cell culture under normoxic conditions, induces expression of erythropoietin. The present invention further relates to novel pharmaceutical compositions comprising a therapeutically or prophylactically effective amount or volume of a cross-linked hemoglobin in a pharmaceutically acceptable carrier, wherein the cross-linked hemoglobin comprises a hemoglobin that is cross-linked intramolecularly with periodate-oxidized ATP, cross-linked intermolecularly with periodate-oxidized adenosine, and conjugated with reduced glutathione. The cross-linked hemoglobin blood substitutes and cross-linked hemoglobins useful for the pharmaceutical compositions of the present invention are capable of (1) stabilizing HIF-1 alpha expression, and/or (2) down regulating NF-kappa B, when tested in a cell culture. The trademark for this product is HEMOTECH™, which is a cross-linked hemoglobin that comprises pure bovine Hb cross-linked with o-adenosine 5'-triphosphate (o-ATP), o-adenosine and reduced glutathione (GSH). More details regarding cross-linked hemoglobins can be found in U.S. Pat. No. 5,439,882 to Feola et al., which is incorporated by reference herein in its entirety.

The invention relates to methods, pharmaceutical compositions and kits useful for subjects in need of acute blood loss therapies. In particular, the invention relates to methods, pharmaceutical compositions and kits useful for subjects with acute blood loss anemia. The subsections below describe in more detail (a) the patient populations which can be treated in accordance with the invention (Section 5.1 and its subsections); (b) novel protocols for acute blood loss therapy encompassed by the invention (Section 5.2); and (c) novel pharmaceutical compositions that may be used in these and other therapies (Section 5.4).

5.1. Subjects in Need of Acute Blood Loss Therapies

Anemia is a condition in which the number of red blood cells or the amount of hemoglobin is low. Severe anemia is clinically defined as having a hemoglobin level of less than 7 g/dL (The Merck Manual of Diagnosis and Therapy. Section 11: Hematology and Oncology. Chapter 127: Anemias, pages 849-850. John Wiley & Sons; 17th edition (Mar. 1, 1999)). Acute blood loss anemia, also known as acute posthemorrhagic anemia, is anemia caused by rapid massive hemorrhage (acute blood loss). Because marrow reserve is limited, anemia may result from massive hemorrhage associated with spontaneous or traumatic eruption or incision of a large blood vessel (e.g., aortic aneurysm), erosion of an artery by lesions (e.g., peptic ulcer, neoplasm), or failure of normal hemostasis. The immediate effects of acute blood loss anemia depends on the duration and volume of hemorrhage.

Acute blood loss anemia is different from chronic blood loss anemia, which is a microcytic anemia caused by prolonged moderate blood loss. For example, chronic anemia can result from a chronically bleeding GI tract lesion (e.g., peptic ulcer, hemorrhoids) or a urologic or gynecologic site. Chronic blood loss anemia can be caused by defective or deficient erythropoiesis, resulting in a microcytic red blood cell population, wherein the average size of circulating erythrocytes is smaller than normal. Defective or deficient erythropoiesis can be a result of iron deficiency, iron-transport deficiency, and/or inadequate or abnormal iron utilization. Chronic blood loss anemia can also be caused by deficiency in vitamin $B_{12}$, folate, or vitamin C. Chronic blood loss anemia can additionally be caused by excessive hemolysis either caused by reticuloendothelial hyperactivity, immunologic abnormalities, alterations of red cell membrane, disorders of red cell metabolism, or defective hemoglobin synthesis (e.g., sickle cell anemia). More discussion on the difference between acute and chronic blood loss anemia can be found in The Merck Manual of Diagnosis and Therapy. Section 11: Hematology and Oncology. Chapter 127: Anemias, pages 849-850. John Wiley & Sons; 17th edition (Mar. 1, 1999), which is incorporated herein by reference in its entirety.

There are many causes of acute blood loss anemia. For example, acute blood loss anemia can be caused by an illness, surgery, or trauma. As such, the subject can be one who has acute blood loss due to an illness as discussed herein in Section 5.1.1 infra.; acute blood loss that occurs during surgery as discussed herein in Section 5.1.2 infra.; or acute blood loss as a result of trauma as discussed herein in Section 5.1.3 infra.

In certain embodiments, the subject may display symptoms that are associated with acute blood loss including, but not limited to, faintness, dizziness, thirst, sweating, weak and rapid pulse, and rapid respiration. In certain other embodiments, the subject can appear to be clinically free of symptoms that are associated with acute blood loss.

In certain embodiments, the subject may display histopathology that are associated with acute blood loss including, but not limited to, hypoxia, and tissue necrosis. In certain other embodiments, the subject can appear to be clinically free of histopathology that are associated with acute blood loss.

In certain embodiments, the subject can be receiving or had already received one or more types of therapy against acute blood loss including, but not limited to, blood transfusion, saline or dextrose infusions, erythropoietin injection.

In certain embodiments, the subject suffers from severe blood loss, or blood loss greater than 33%, or one-third, of blood volume. In certain other embodiments, the subject suffers from moderate blood loss, or blood loss between 20% to 33% of blood volume. In certain other embodiments, the subject suffers from mild blood loss, or blood loss less than 20% of blood volume. Normal blood volume is about 8% of body weight, or about 5 liter, for a human subject.

In certain embodiments, the subject has less than 10 g/dL, 9 g/dL, 8 g/dL, 7 g/dL, 5 g/dL, 4 g/dL, 3 g/dL, 2 g/dL or less hemoglobin. In one embodiment, the subject has less than 7 g/dL hemoglobin.

As used herein, the terms "subject" and "patient" are used interchangeably. The subject can be an animal. In particular, the subject can be a mammal such as a non-primate (e.g., a cow, pig, horse, cat, dog, rat, and mouse) or a primate (e.g., a monkey, such as a cynomolgous monkey, chimpanzee, and a human).

Preferably, the subject is a human. In one embodiment, the subject is a human infant or a human infant born prematurely. In another embodiment, the subject is a human child. In another embodiment, the subject is a human adult. In yet another embodiment, the subject is an elderly human. As used herein, the term "human infant" refers to a human less than 24 months, preferably less than 16 months, less than 6 months, less than 3 months, less than 2 months, or less than 1 month of age. As used herein, the term "human child" refers to a human between 24 months of age and 18 years of age. As used herein, the term "human adult" refers to a human 18 years of age or older. As used herein, the term "elderly human" refers to a human 55 years of age or older.

In certain situations, the subject is immunocompromised or immunosuppressed. For example, the subject can be an HIV-positive or AIDS patient.

5.1.1 Acute Blood Loss Due to an Illness

The subject can be one who has acute blood loss due to an illness. In one embodiment, the subject can be suffering from or diagnosed with an illness that causes acute blood loss. In another embodiment, the subject can be predisposed to or at risk of developing an illness that causes acute blood loss as a result of genetic factors (e.g., family history) and/or environmental factors (e.g., diet).

As used herein, the term "illness" is used interchangeable with the term "disease." An illness that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract). Examples of illness that can cause acute blood loss include, but are not limited to, hemorrhagic diseases, ulcer, lesions, ruptured blood vessels, and ruptured aneurysms.

Some hemorrhagic diseases are present at birth and are caused by rare inherited disorders. For example, the subject can be a hemophiliac who lacks either the blood clotting protein factor VIII (hemophilia A) or factor IX (hemophilia B), and thus, suffers from poor blood clotting and/or continuous, uncontrollable bleeding. The subject can be a hemophilic female who has begun to menstruate and bleeds uncontrollably during each menstruation (see, e.g., Quick et al. Hemophilic condition in a girl. AMA Am J Dis Child. June 1953; 85(6):698-705). A hemorrhagic disease can also develop during certain illnesses (e.g., vitamin K deficiency, severe liver disease, von Willebrand's disease, leukemia, bone marrow problems, disseminated intravascular coagulation, pregnancy-associated eclampsia, exposure to snake venom), or treatments (e.g., the use of anticoagulant drugs such as aspirin, heparin or warfarin, or prolonged use of antibiotics). The subject can be a newborn who has vitamin K deficiency (The Merck Manual of Diagnosis and Therapy. Section 1: Nutritional Disorders. Chapter 3: Vitamin Deficiency, Dependency, And Toxicity, page 42. John Wiley & Sons; 17th edition (Mar. 1, 1999).

The subject can be administered the blood substitutes and pharmaceutical compositions of the present invention before, during and/or after the illness. The timing and amounts/volumes of the blood substitutes and pharmaceutical compositions administered can be selected by the skilled practitioner using ordinary skill taking into account, for example, the degree of blood loss in the subject.

5.1.2. Acute Blood Loss that Occurs During Surgery

The subject can be one who has acute blood loss that occurs during surgery. In one embodiment, the subject can be undergoing a surgery that can cause acute blood loss. In another embodiment, the subject can be scheduled to undergo a surgery that can cause acute blood loss. In another embodiment, the subject can be predisposed to or at high risk of needing a surgery that can cause acute blood loss as a result of genetic factors (e.g., family history) and/or environmental factors (e.g., diet).

As used herein, the term "surgery" is used interchangeable with the term "operation." A surgery that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract). Examples of surgeries that can cause acute blood loss include, but are not limited to, an elective surgery.

There are many different types of surgery including, but is not limited to, optional or elective surgery, required surgery, and urgent or emergency surgery. An optional or elective surgery is a procedure one chooses to have, which may not necessarily be essential to continue a good quality of life. An example would be an orthopedic surgery, which is a surgery concerned with acute, chronic, traumatic, and recurrent injuries and other disorders of the musculoskeletal system. Another example would be to have an unsightly mole or wart removed. A required surgery is a procedure which needs to be done to ensure quality of life in the future. Required surgery, unlike emergency surgery, does not necessarily have to be done immediately. An example would be having kidney stones removed if other forms of medication and treatments are not working. Urgent or emergency surgery is done in reaction to an urgent medical condition, such as acute appendicitis.

Many surgical procedures have been reported to be associated with a high risk of hemorrhage or blood loss. For examples, cerebral amyloid angiopathy (see, e.g., Matkovic et al. Surgical risk of hemorrhage in cerebral amyloid angiopathy. Stroke. April 1991; 22(4):456-61); repair of a brain aneurysm (see, e.g., Mayberg et al. Guidelines for the management of aneurysmal subarachnoid hemorrhage. A statement for healthcare professionals from a special writing group of the Stroke Council, American Heart Association. Stroke. November 1994; 25(11):2315-28; Tsutsumi et al. Risk of subarachnoid hemorrhage after surgical treatment of unruptured cerebral aneurysms. Stroke. 1999; June; 30(6): 1181-4; and Wirth F P. Surgical treatment of incidental intracranial aneurysms. Clin Neurosurg. 1986; 33:125-35); radiosurgery for arteriovenous malformations (see, e.g., Friedman et al. The risk of hemorrhage after radiosurgery for arteriovenous malformations. J Neurosurg. June 1996; 84(6):912-9; Hunt et al. Surgical risk as related to time of intervention in the repair of intracranial aneurysms. J Neurosurg. January 1968; 28(1): 14-20); endovascular treatment of posteri or circulation aneurysms (see, e.g., Guglielmi et al. Endovascular treatment of posterior circulation aneurysms by electrothrombosis using electrically detachable coils. J Neurosurg. October 1992; 77(4):515-24); proliferative vitreoretinopathy (see, e.g., Bonnet et al. Surgical risk factors for severe postoperative proliferative vitreoretinopathy (PVR) in retinal detachment with grade B PVR. Graefes Arch Clin Exp Ophthalmol. December 1995; 233(12):789-91); lipoma excision (see, e.g., Rodriguez et al. Colonic lipoma as a source of massive hemorrhage. Report of a case. Dis Colon Rectum. November 1990; 33(11):977-9); and sinus surgery (see, e.g., Schnipper et al. Management of intracranial complications of sinus surgery. Otolaryngol Clin North Am. April 2004; 37(2): 453-72, ix). As such, the subject can be one who is undergoing, scheduled to undergo, or has undergone cerebral amyloid angiopathy; repair of a brain aneurysm; radiosurgery for arteriovenous malformations; endovascular treatment of posteri or circulation aneurysms; proliferative vitreoretinopathy; lipoma excision; or sinus surgery.

The subject can be administered the blood substitutes and pharmaceutical compositions of the present invention before, during and/or after the surgery. The timing and amounts/volumes of the blood substitutes and pharmaceutical compositions administered can be selected by the skilled practitioner using ordinary skill taking into account, for example, the degree of blood loss in the subject.

5.1.3. Acute Blood Loss from Trauma

The subject can be one who has acute blood loss from trauma. In one embodiment, the subject is suffering from or diagnosed with a trauma that can cause acute blood loss. In another embodiment, the subject can be predisposed to or at risk of suffering a trauma that causes acute blood loss as a result of genetic factors (e.g., triple-X syndrome) and/or environmental factors (e.g., living in a high crime neighborhood).

As used herein, the term "trauma" is used interchangeable with the term "injury." A trauma that causes acute blood loss can involve any type of cell (e.g., somatic cell, germ cell, embryonic cell, stem cell), tissue (e.g., bone, muscle, connective, blood), and/or organ (e.g., brain, kidney, lung, heart, pancreas, prostate, ovary, uterus, gastrointestinal tract). Examples of trauma that can cause acute blood loss include, but are not limited to, a burn, a gunshot wound, and a stab wound.

There are many different types of trauma including, but is not limited to, accidental injury and or criminal injury. An accidental injury is injury sustain in any type of accident (e.g., accidental death, automobile accident injury, whiplash, drowning, fall, sports injury, burn, machinery accident, suffocation, natural accident, accidental eye injury, occupational injury, toy-related injury). Criminal injury is injury caused by criminal activity (e.g., child abuse, homicide, assault). In particular, gunshot wound and stab wound.

The subject can be administered the blood substitutes and pharmaceutical compositions of the present invention before, during and/or after the trauma. The timing and amounts/volumes of the blood substitutes and pharmaceutical compositions administered can be selected by the skilled practitioner using ordinary skill taking into account, for example, the degree of blood loss in the subject.

5.2. Acute Blood Loss Therapies

The methods of the present invention comprise administering to subjects in need thereof one or more blood substitutes and/or pharmaceutical compositions in an amount or volume effective to elevate blood volume and counter hypoxia associated with the acute blood loss. The blood substitute used can be selected based on its ability to induce expression of erythropoitin in cell culture under normoxic conditions. When used in subjects, the blood substitute can be shown to increase erythropoiesis under normoxic conditions as measured by (a) a decrease in the doubling time of the subject's hematocrit or hemoglobin, or (b) an increase in the subject's circulating erythropoietin level. In particular, the methods of the present invention comprise administering to subjects in need thereof a therapeutically or prophylactically effective amount or volume of one or more blood substitutes and/or pharmaceutical compositions discussed herein Sections 5.3 (and its subsection) and 5.4 infra., respectively. The invention provides methods for treating or preventing acute blood loss anemia. For example, the invention provides methods for treating or preventing acute blood loss due to an illness (see Section 5.2.1 supra.), or that occurs during surgery (see Section 5.1.2 supra.), or from trauma (see Section 5.1.3 supra.).

The blood substitutes of the present invention is especially useful for acute blood loss therapies for a number of reasons. First and most importantly, the blood substitutes of the present invention not only elevates blood volume to compensate for fluid loss that could cause shock during acute blood loss and counteract hypoxia in the patient, but also stimulate erythropoiesis under normoxic conditions. This can be very advantageous for treating acute blood loss patients since such subjects sometimes need multiple blood transfusions to replace the blood lost during and after the blood losing event as well as to improve and/or maintain hematocrit level. The blood substitutes of the present invention can induce erythropoiesis at a faster and higher rate than other blood substitutes and donor blood, and thus, reduce the number of administrations.

Second, the blood substitutes of the present invention is suitable and readily for use in acute blood loss therapies because it does not need to be tested to determine its suitability for transfusion and compatibility to the recipient. Also, the blood substitutes of the present invention will not trigger the many complications associated with immunological components that are present in donor blood (e.g., hemolysis of RBCs, allergic reactions, transfusion-related acute lung injury, graft-vs.-host disease, bacterial contamination, viral disease transmission, etc.).

The therapeutic and prophylactic methods of the invention improves many aspects of the hemodynamics or physical aspects of blood circulation in a subject. More particularly, the physical presence of the blood substitutes and pharmaceutical compositions used in the methods of the invention can improve a subject's hemodynamics. For example, the therapeutic and prophylactic methods of the invention elevate the blood volume of a subject. In specific embodiments, the blood volume is elevated by 5%, 10%, 20%, 50%, 100%, 200%, 500% or more. In specific embodiments, the blood volume is elevated by 0.1 liter, 0.5 liter, 1.0 liter, 1.5 liter, 2.0 liter or more. Blood volume can be measured using methods well known to one skilled in the art. For example, blood volume can be measured using a catheter connected with a disposable, small volume blood pressure transducer (Ohmeda, Pte, Ltd, Singapore).

The therapeutic and prophylactic methods of the invention can also restore blood flow in a subject. For humans, normal blood flow is 250 to 300 ml/min. In specific embodiments, 5%, 10%, 20%, 30%, 40%, 50%, 60%, 70%, 80%, 90%, or 100% of blood flow is restored. Blood flow can be measured using methods well known to one skilled in the art. For example, blood flow can be measured using a catheter connected with a disposable, small volume blood pressure transducer (Ohmeda, Pte, Ltd, Singapore).

The therapeutic and prophylactic methods of the invention can also restore tissue oxygenation level in a subject. Tissue oxygenation level is not uniform over the entire body. Tissue oxygenation level can be improved by maximizing tissue/organ perfusion. In specific embodiments, 5%, 10%, 20%, 30%, 40%, 50%, 60%, 70%, 80%, 90%, or 100% of tissue oxygenation level is restored. Tissue oxygenation levels can be measured using methods well known to one skilled in the art. For example, tissue oxygenation levels can be continuously recorded by connecting the interface of the DO-166 probe with Microcomputer (pH-version 6071, Lazar Research Laboratories) and chart recorder of the Cardiomax Circulatory System Computer.

The therapeutic and prophylactic methods of the invention can also restore a hemodynamic parameter in a subject. Hemodynamic parameters include, but are not limited to, cardiac output (CO; in ml/min; cardiac index (CI) in ml/min/100 g body weight), stroke volume (SV; in ml/beat/100 g body weight), mean arterial pressure (MAP; in mmHg), pulse pressure (PP; in mmHg), heart rate (HR; in beats/min), total peripheral resistance (TPR; in $(dyn/sec/cm^{-5}) \times 10^3$), and blood temperature. For humans, normal cardiac output is 5 to 6 liters every minute; normal cardiac index is 2.5 to 4 liters per minute; normal stroke volume is 60 to 130 ml per beat; normal mean arterial pressure is 70 to 90 mm Hg; normal pulse pressure is 20 to 60 mm Hg; normal heart rate is 60 to 100 beats per minute; normal total peripheral resistance is 770 to 1500 $dyn/sec/cm^{-5}$; and normal blood temperature is 37° C. In specific embodiments, 5%, 10%, 20%, 30%, 40%, 50%, 60%, 70%, 80%, 90%, or 100% of one or more hemodynamic parameters is restored. Hemodynamic parameters can be measured using methods well known to one skilled in the art. For example, hemodynamic parameters can be measured using a fully automatic, Cardiomax Circulatory System Computer (Columbus Instruments, Columbus, Ohio).

The therapeutic and prophylactic methods of the invention also counter hypoxia associated with the acute blood loss in a subject. In specific embodiments, hypoxia is reduced by 5%, 10%, 20%, 50%, 100%, 200%, 500%, 1000% or more. Hypoxia can be measured using methods well known to one skilled in the art. For example, hypoxia can be measured using tissue oxygenation level as a proxy.

The therapeutic and prophylactic methods of the invention can also reverse a hemorrhagic shock in a subject. Hemorrhagic shock is characterized by approximately a 66% drop in cardiac index, approximately 67% drop in mean arterial pressure with significant increase in TPR, and approximately 78% reduction in tissue oxygenation.

The therapeutic and prophylactic methods of the invention can also improve endogenous production of erythropoietin, which is responsible for erythropoiesis (i.e., red blood cell production), in a subject. For example, the therapeutic and prophylactic methods of the invention can increase EPO or EPO synthesis in a subject. Erythropoietin (EPO) is a glycoprotein (46 kD) hormone produced by specialized cells in the kidneys that regulates the production of red blood cells in the marrow. In specific embodiments, circulating EPO or EPO synthesis is increased by 5%, 10%, 20%, 30%, 40%, 50%, 60%, 70%, 80%, 90%, 100%, 200%, 500%, 1000% or more. In specific embodiments, the circulating EPO level is increased by 5 mU/ml, 10 mU/ml, 20 mU/ml, 50 mU/ml, 100 mU/ml, 150 mU/ml, 200 mU/ml or more. Circulating EPO level and EPO synthesis can be measured using methods well known to one skilled in the art. For example, circulating EPO level and EPO synthesis can be measured in the cell culture supernatant using a highly specific Quantikine In Vitro Diagnostic Human Erythropoietin ELISA (R&D Systems Inc., Minneapolis, Minn.) or a EPO-Trac $^{125}$I RIA Kit (INCSTAR Corp. now Dia Sorin S.p.A., Sallugi, Italy).

The therapeutic and prophylactic methods of the invention can also restore hematocrit level in a subject. Hematocrit, which is the ratio of the volume of red blood cells to the volume of whole blood, expressed as a percentage, is a powerful indicator of erythropoiesis in blood samples containing plasma free hemoglobin. Normal hematocrit is 47±5% for an adult male, and 42±5% for an adult female (The Merck Manual of Diagnosis and Therapy. Section 11: Hematology and Oncology. Chapter 127: Anemias, page 854. John Wiley & Sons; 17th edition (Mar. 1, 1999)). In specific embodiments, 5%, 10%, 20%, 30%, 40%, 50%, 60%, 70%, 80%, 90%, or 100% of hematocrit level is restored. Hematocrit can be measured using methods well known to one skilled in the art. For example, hematocrit can be measured using heparinized micro-hematocrit capillary tubes (Fisher Scientific, Houston, Tex.) and micro-hematocrit centrifuge (Damon ICE Division, Needham, Mass.).

The therapeutic and prophylactic methods of the invention can also restore hemoglobin level in a subject. Hemoglobin is the iron-containing oxygen-transport metalloprotein in red blood cells (RBCs). Normal hemoglobin is 16±2 g/dL for an adult male, and 14±2 g/dL for an adult female (The Merck Manual of Diagnosis and Therapy. Section 11: Hematology and Oncology. Chapter 127: Anemias, page 854. John Wiley & Sons; 17th edition (Mar. 1, 1999)). In specific embodiments, 5%, 10%, 20%, 30%, 40%, 50%, 60%, 70%, 80%, 90%, or 100% of hemoglobin level is restored. Hemoglobin can be measured using methods well known to one skilled in the art. For example, hemoglobin can be measured using HemoCue B-Hemoglobin Photometer (HemoCue Corp., Angelholm, Sweden).

The therapeutic and prophylactic methods of the invention can also stabilize HIF-1 alpha expression in a subject. In specific embodiments, 5%, 10%, 20%, 30%, 40%, 50%, 60%, 70%, 80%, 90%, or 100% of HIF-1 alpha is stabilized. HIF-1 alpha stabilization can be measured using methods well known to one skilled in the art. HIF-1 alpha stabilization can be measured using a high-throughput TransAM ELISA based assay (Active Motif, Carlsbad, Calif.).

The therapeutic and prophylactic methods of the invention can also down regulate NF-kappa B expression in a subject. In specific embodiments, 5%, 10%, 20%, 30%, 40%, 50%, 60%, 70%, 80%, 90%, or 100% of NF-kappa B expression is down regulated. NF-kappa B activation can be measured using methods well known to one skilled in the art. For example, NF-kappa B activation can be measured using a TransAM™ NF-kappa B p65 transcription Factor Assay Kit (Active Motif, Carlsbad, Calif.).

The therapeutic and prophylactic methods of the invention can also reduce apoptosis of pro-erythroblasts in a subject. In specific embodiments, the apoptosis of pro-erythroblasts is reduced by 5%, 10%, 20%, 30%, 40%, 50%, 60%, 70%, 80%, 90%, or 100%. Apoptotic events can be measured using methods well known to one skilled in the art. For example, early and late apoptotic events can be evaluated using Annexin V-FITC and propidium iodide fluorescent probes, respectively (Sigma Chemical).

The therapeutic and prophylactic methods of the invention can also reduce production of anti-erythropoietic inflammatory cytokines in a subject. Anti-erythropoietic inflammatory cytokines include, but are not limited to, TNF-alpha, TGF-beta 1, IL-1, IL-6, etc. In specific embodiments, the production of one or more anti-erythropoietic inflammatory cytokines is reduced by 5%, 10%, 20%, 30%, 40%, 50%, 60%, 70%, 80%, 90%, or 100%. Anti-erythropoietic inflammatory cytokines production can be measured using methods well known to one skilled in the art. For example, TNF-alpha can be measured using a TNF-alpha human EIA Kit (Cayman Chemical, Ann Arbor, Mich.), and TGF-beta 1 can be measured using a Human TGF-beta 1 Quantikine Immunoassay (R&D Systems).

As used herein, the terms "an effective amount" and "an effective volume" mean an amount and volume, respectively, sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the one or more blood substitutes and/or pharmaceutical compositions of the invention.

As used herein, the terms "a therapeutically effective amount" and "a therapeutically effective volume" refer to that amount and volume, respectively, sufficient to provide some improvement or benefit to a subject with acute blood loss. For example, the therapeutically effective amount or therapeutically effective volume can refer to an amount or volume of a blood substitute or pharmaceutical composition of the present invention sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the blood substitute or pharmaceutical composition. The therapeutically effective amount or therapeutically effective volume may also refer to an amount or volume of the blood substitutes or pharmaceutical compositions of the present invention that provides a therapeutic benefit in the treatment or management of the symptoms or histopathology associated with acute blood loss. Further, the therapeutically effective amount or therapeutically effective volume with respect to a blood substitute or pharmaceutical composition of the present invention means that amount or volume of the blood substitute or pharmaceutical composition alone, or in combination with other therapies, that provides a therapeutic benefit in the treatment, management, or amelioration of acute blood loss or the symptoms or histopathology associated with acute blood loss.

As used herein, the terms "a prophylactically effective amount" and "a prophylactically effective volume" refer to that amount or volume, respectively, sufficient to delay or prevent a subject from having acute blood loss. For example, the prophylactically effective amount or prophylactically effective volume can refer to an amount or volume of a blood substitute or pharmaceutical composition of the present invention sufficient to elevate blood volume, restore blood flow, restore tissue oxygenation level, restore a hemodynamic parameter, counter hypoxia associated with acute blood loss, increase circulating EPO or EPO synthesis, restore hematocrit level, restore hemoglobin level, stabilize HIF-1 alpha, down regulate NF-kappa B, reduce apoptotic events of pro-erythroblasts, and/or reduce the production of anti-erythropoietic inflammatory cytokines in a subject being administered the blood substitute or pharmaceutical composition. The prophylactically effective amount or prophylactically effective volume may also refer to an amount or volume of the blood substitutes or pharmaceutical compositions of the present invention that provides a prophylactic benefit in the treatment or management of the symptoms or histopathology associated with acute blood loss. Further, the prophylactically effective amount or prophylactically effective volume with respect to a blood substitute or pharmaceutical composition of the present invention means that amount or volume of the blood substitute or pharmaceutical composition alone, or in combination with other therapies, that provides a prophylactic benefit in the treatment, management, or amelioration of acute blood loss or the symptoms or histopathology associated with acute blood loss.

As used herein, the terms "treat," "treating" and "treatment of" (or grammatically equivalent terms) with respect to acute blood loss refer to reducing or eliminating acute blood loss or the symptoms or histopathology associated with acute blood loss.

As used herein, the terms "prevent," "preventing" and "prevention of" (or grammatically equivalent terms) with respect to acute blood loss refer to delaying or preventing acute blood loss or the symptoms or histopathology associated with acute blood loss.

The therapeutically or prophylactically effective amount or volume, and the frequency of administration, will vary with the type and severity of acute blood loss, or symptoms or histopathology associated with acute blood loss. The therapeutically or prophylactically effective amount or volume, and the frequency of administration, will also vary with the subject treated. For example, the therapeutically or prophylactically effective amount or volume, and the frequency of administration, will vary according to the age, gender, body weight, and response of the subject.

In specific embodiments, the total daily amount of a blood substitute or pharmaceutical composition of the present invention to be administered to a subject with acute blood loss is 1 g, 2 g, 3 g, 4 g, 5 g, 6 g, 7 g, 8 g, 9 g, 10 g, 20 g, 50 g, 100 g, 200 g, 500 g, 1000 g or more. In a preferred embodiment, the total daily amount of a blood substitute or pharmaceutical composition of the present invention to be administered to a subject with acute blood loss is in the range of 7 g to 700 g, preferably 7 g to less than 122.5 g or from greater than 122.5 g to 700 g, administered in single or divided dose.

In specific embodiments, the total daily volume of a blood substitute or pharmaceutical composition of the present invention to be administered to a subject with acute blood loss is 0.01 liter, 0.05 liter, 0.1 liter, 0.2 liter, 0.5 liter, 1.0 liter, 1.5 liter, 2.0 liter or more. In a preferred embodiment, the total daily amount of a blood substitute or pharmaceutical composition of the present invention to be administered to a subject with acute blood loss is in the range of 0.1 liter to 1 liter, preferably 0.6 liter, administered in single or divided dose.

It may be necessary to use amounts and volumes outside these number and ranges in some cases as will be apparent to those skilled in the art.

The length of time for a course of treatment can be at least 6 hours, at least 12 hours, at least 24 hours, at least 1 day, at least 2 days, at least 3 days, at least 4 days, at least 5 days, at least 6 days, at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. In certain embodiments, a blood substitute or pharmaceutical composition of the present invention can be administered for a period of time until the acute blood loss ceases or is under control, or when symptom of acute blood loss has regressed partially or completely.

The blood substitute and pharmaceutical compositions of the present invention can be administered as a dietary supplement for as long as 6 months, or in accordance with recommended length of use under the Dietary Supplement Health and Education Act (DSHEA) or other government or industry guidelines. Further, it is noted that the nutritionist, dietician, clinician or treating physician will know how and when to interrupt, adjust, or terminate use of the blood substitutes and pharmaceutical compositions of the present invention as a medicament or dietary supplement in conjunction with individual patient response.

The blood substitutes and pharmaceutical compositions of the present invention can be administered adjunctively with any of the conventional treatment modalities, such as but not limited to, blood transfusion, saline or dextrose infusions, erythropoietin injection.

In certain embodiments, one or more blood substitutes and/or pharmaceutical compositions of the present invention is/are administered sequentially. In certain other embodiments, one or more blood substitutes and/or pharmaceutical compositions of the present invention is/are administered simultaneously.

The therapeutic and prophylactic effects of the methods of the invention can be monitored on a regular basis by any methods known to one skilled in the art. For example, blood volume, hypoxia associated with acute blood loss, hematocrit level, hemoglobin level, hemodynamic parameters, blood flow, tissue oxygenation level, circulating EPO level, EPO synthesis, HIF-1 alpha expression, NF-kappa B expression, apoptotic events of pro-erythroblasts, anti-erythropoietic inflammatory cytokine level, and/or general health, physical health, and/or emotional health of the subjects after treatment can be measured at 1 week, 2 weeks, 3 weeks, or up to 4 weeks of post-treatment. Doctor's visits can take place before, during, and/or after the course of treatment, for example, on a daily, weekly, bi-weekly, monthly, or yearly basis.

5.3. Blood Substitutes

The blood substitutes of the present invention are preferably pathogen-free, non-toxic, non-immunogenic, non-pyrogenic, and have an extended shelf-life.

In particular, the blood substitutes useful for the methods and pharmaceutical compositions of the present invention are capable of (1) inducing expression of erythropoietin as tested in a cell culture under normoxic conditions, and/or (2) inducing erythropoiesis under normoxic conditions as measured by (a) a decrease in the doubling time of the subject's hematocrit or hemoglobin, or (b) an increase in the subject's circulating erythropoietin level. Any blood substitutes which exhibit these characteristics can be used in the methods and pharmaceutical compositions of the present invention.

Any blood substitutes, including currently known and/or commercially available blood substitutes, which exhibit the above-discussed characteristics can be used in the methods and pharmaceutical compositions of the present invention. For example, it was discovered that a good blood substitute for use in the invention is a cross-linked hemoglobin that comprises pure bovine Hb cross-linked with o-adenosine 5'-triphosphate (o-ATP), o-adenosine and reduced glutathione (GSH) (e.g., HEMOTECH™) can elevate blood volume and counter hypoxia associated with the acute blood loss, as well as (1) induce expression of erythropoietin as tested in a cell culture under normoxic conditions, and/or (2) induce erythropoiesis under normoxic conditions as measured by (a) a decrease in the doubling time of the subject's hematocrit or hemoglobin, or (b) an increase in the subject's circulating erythropoietin level. Other blood substitutes such as HEMASSIST™ (Baxter Healthcare, Round Lake, Ill.), HEMOLINK™ (Hemosol, Inc., Toronto, Canada), OPTRO™ (Somatogen, Boulder, Colo.), HEMOPURE® (Biopure Inc., Cambridge, Mass.), POLYHEME® (Northfield Laboratories Inc., Evanston, Ill.), as discussed above, and HEMOSPAN® (Sangart, Inc., San Diego, Calif.), which is harvested from outdated human blood and combined with polyethylene glycol (PEG) to eliminate the toxicity of free hemoglobin, and HEMOZYME® (SynZyme Technologies, LLC, Irvine, Calif.), which consists of a hemoglobin carrier and CNO complex, are not known to be capable of inducing erythropoiesis under normoxic conditions. Nevertheless, it is contemplated that they can be adapted to induce the production of endogenous erythropoietin so that erythropoiesis in a subject and thus, stimulates erythropoisis.

In certain embodiments, the blood substitutes useful for the methods and pharmaceutical compositions of the present invention are capable of inducing expression of erythropoietin as tested in a cell culture under normoxic conditions. In specific embodiments, expression of erythropoietin is induced at 5% or less, 10%, 20%, 50%, 100%, 200%, 500% or more of baseline level. The expression of erythropoietin can be measured by any methods well known to one skilled in the art.

In certain embodiments, the blood substitutes useful for the methods and pharmaceutical compositions of the present invention are capable of inducing erythropoiesis under normoxic conditions as measured by a decrease in the doubling time of the subject's hematocrit. In specific embodiments, the doubling time of the subject's hematocrit is decreased by 5% or less, 10%, 20%, 50%, 100%, 200%, 500% or more. In specific embodiments, the doubling time of the subject's hematocrit is decreased by 6 hours, 12 hours, 1 day, 2 days, 3 days, 4 days, 5 days, 6 days, 7 days, 8 days, 9 days, 10 days, 20 days or more. In specific embodiments, the doubling time of the subject's hematocrit is less than 30 days, 20 days, 10 days, 9 days, 8 days, 7 days, 6 days, 5 days, 4 days, 3 days, 2 days, 1 days, 12 hours, or 6 hours. In a preferred embodiment, the doubling time of the subject's hematocrit is less than 3 days. The doubling time of the subject's hematocrit can be measured by any methods well known to one skilled in the art.

In certain embodiments, the blood substitutes useful for the methods and pharmaceutical compositions of the present invention are capable of inducing erythropoiesis under normoxic conditions as measured by a decrease in the doubling time of the subject's hemoglobin. In specific embodiments, the doubling time of the subject's hemoglobin is decreased by 5% or less, 10%, 20%, 50%, 100%, 200%, 500% or more. In specific embodiments, the doubling time of the subject's hemoglobin is decreased by 6 hours, 12 hours, 1 day, 2 days, 3 days, 4 days, 5 days, 6 days, 7 days, 8 days, 9 days, 10 days, 20 days or more. In specific embodiments, the doubling time of the subject's hemoglobin is less than 30 days, 20 days, 10 days, 9 days, 8 days, 7 days, 6 days, 5 days, 4 days, 3 days, 2 days, 1 days, 12 hours, or 6 hours. In a preferred embodiment, the doubling time of the subject's hemoglobin is 7 days. The doubling time of the subject's hemoglobin can be measured by any methods well known to one skilled in the art.

In certain embodiments, the blood substitutes useful for the methods and pharmaceutical compositions of the present invention are capable of inducing erythropoiesis under normoxic conditions as measured by an increase in the subject's circulating erythropoietin level. In specific embodiments, the subject's circulating erythropoietin level is increased by 5% or less, 10%, 20%, 50%, 100%, 200%, 500% or more. In specific embodiments, the subject's circulating erythropoietin level is increased by 5 mU/ml, 10 mU/ml, 20 mU/ml or more. In specific embodiments, the subject's circulating erythropoietin level is 20 mU/ml, 50 mU/ml, 100 mU/ml, 200 mU/ml, 500 mU/ml, 1000 mU/ml or more. In a preferred embodiment, the subject's circulating erythropoietin level is 15±5 mU/ml. The subject's circulating erythropoietin level can be measured by any methods well known to one skilled in the art.

According to one aspect of the present invention, the blood substitutes are cross-linked hemoglobins discussed in Section 5.3.1 infra., or the novel compositions discussed in Section 5.4 infra.

5.3.1. Cross-Linked Hemoglobins

The cross-linked hemoglobins of the present invention include, but are not limited to, those described in U.S. Pat. No. 5,439,882 to Feola et al, which is incorporated by reference herein in its entirety. In particular, a cross-linked hemoglobin of the present invention include HEMOTECH™.

The cross-linked hemoglobins comprise a hemoglobin that is cross-linked intramolecularly with periodate-oxidized ATP (o-ATP), and cross-linked intermolecularly with periodate-oxidized adenosine (o-adenosine) to form a polyhemglobin.

The hemoglobin and periodate-oxidized ATP in the cross-linked hemoglobins of the present invention can be at a molar ratio of 1:1 to 1:3, or any ranges in between.

The hemoglobin and periodate-oxidized adenosine in the cross-linked hemoglobins of the present invention can be at a molar ratio of 1:1 to 1:10, or any ranges in between.

The hemoglobin and periodate-oxidized ATP in the cross-linked hemoglobins of the present invention can be at a molar ratio of 1:1 to 1:3, or any ranges in between, and the hemoglobin and periodate-oxidized adenosine in the cross-linked hemoglobins of the present invention can be at a molar ratio of 1:1 to 1:10, or any ranges in between.

The hemoglobin in the cross-linked hemoglobins of the present invention is further conjugated with reduced glutathione. Addition of reduced glutathione stops the cross-linking reaction of the hemoglobin with periodate-oxidized adenosine.

In specific embodiments, the hemoglobin and reduced glutathione in the cross-linked hemoglobins of the present invention are at a molar ratio of 1:1 to 1:20, or any ranges in between.

The periodate-oxidized ATP, periodate-oxidized adenosine, and reduced glutathione can be cross-linked to the hemoglobin by any methods known to one skilled in the art (see, e.g., U.S. Pat. No. 5,439,882 to Feola et al.).

Preferably, the hemoglobin is bovine hemoglobin. However, other sources of hemoglobin may also be utilized herein. Preferably, the cross-linked hemoglobins of the present invention comprise less than about 50%, 30%, 20%, 10%, 5%, 1% or less, or no met-hemoglobin.

The cross-linked hemoglobins of the present invention preferably have about 130 to 390 kilodalton molecular weight, and more preferably about 190 to 260 kilodalton molecular weight, and at a maximum, exceeding 1000 kilodalton molecular weight.

The hemoglobin, periodate-oxidized ATP, periodate-oxidized adenosine, and reduced glutathione may be obtained from commercial sources (Sigma Chemical Co., St. Louis, Mo.) or prepared according to the methods described in U.S. Pat. No. 5,439,882 to Feola et al., which is incorporated by reference herein in its entirety.

The cross-linked hemoglobins of the present invention can be dissolved in a non-electrolytic aqueous solution. Examples of non-electrolytes that may be added to the aqueous solution of the cross-linked hemoglobins of the present invention are human albumin, different plasma fractions, and plasma. However, any non-electrolyte that is pharmaceutically-acceptable and does not interfere with the oxygen-carrying function of the cross-linked hemoglobins of the present invention may also be utilized, such as dextran and hydroxyethyl starch.

The cross-linked hemoglobins of the present invention can be made by methods including, but not limited to, those described in U.S. Pat. No. 5,439,882 to Feola et al, which is incorporated by reference herein in its entirety.

For example, the cross-linked hemoglobins of the present invention are made by a method comprising the following steps:

(a) separating whole blood into a leukocyte-erythrocyte mixture, platelets and plasma and suspending the thus obtained mixture in an aqueous solution;

(b) cooling the aqueous solution comprising the leukocyte-erythrocyte mixture to aggregate the leukocytes and removing the leukocyte aggregate to obtain a substantially leukocyte-free solution;

(c) dialyzing the substantially leukocyte-free solution against a hypotonic solution to extract hemoglobin from erythrocytes in the substantially leukocyte-free solution and separating out the erythrocytes from the extracted hemoglobin in the substantially leukocyte-free solution by ultrafiltration under increased hydrostatic pressure to obtain an extracted hemoglobin solution;

(d) converting the extracted hemoglobin in the extracted hemoglobin solution to carboxy-hemoglobin to obtain a carboxy-hemoglobin solution;

(e) pasteurizing the carboxy-hemoglobin solution to denature and precipitate non-heme proteins;

(f) removing phospholipids and precipitated non-heme proteins from the carboxy-hemoglobin solution;

(g) removing endotoxins from the carboxy-hemoglobin solution by affinity chromatography;

(h) concentrating the carboxy-hemoglobin in the carboxy-hemoglobin solution to a concentration of about 10 g/dL to obtain a concentrated carboxy-hemoglobin solution;

(i) reacting the carboxy-hemoglobin in the concentrated carboxy-hemoglobin solution with o-ATP to effect predominantly intramolecular cross-linking of carboxy-hemoglobin, thus obtaining an intramolecularly cross-linked carboxy-hemoglobin solution;

(j) reacting the o-ATP carboxy-hemoglobin with o-adenosine in an amount effective to effect predominantly intermolecular cross-linking of carboxy-hemoglobin, thus obtaining an intermolecularly and intramolecularly cross-linked carboxy-hemoglobin solution, and adding glutathione to the intermolecularly and intramolecularly cross-linked carboxy-hemoglobin solution to quench the o-adenosine cross-linking reaction; and (k) converting the cross-linked carboxy-hemoglobin in the intermolecularly and intramolecularly cross-linked carboxy-hemoglobin solution to cross-linked oxy-hemoglobin.

In a specific embodiment, the leukocyte-erythrocyte mixture is separated from the platelets and the plasma in step (a) by centrifuging whole blood. In another specific embodiment, the leukocyte aggregate in step (b) is removed by filtration. In another specific embodiment, the phospholipids and the precipitated non-heme proteins are removed from the carboxy-hemoglobin solution in step (f) by solvent extraction. In another specific embodiment, the concentrated carboxy-hemoglobin solution in step (h) is concentrated by dialysis against an about normotonic solution.

5.4. Pharmaceutical Compositions and Kit

The present invention also relates to novel pharmaceutical compositions comprising certain concentrations or volumes of blood substitutes that can be used in the methods of the invention, or other therapeutic methods. For example, such novel compositions can comprise a therapeutically effective amount of from 7 g to less than 122.5 g of a cross-linked hemoglobin blood substitute in a pharmaceutically acceptable carrier, wherein the cross-linked hemoglobin blood substitute, when tested in a cell culture under normoxic conditions, induces expression of erythropoietin. Alternatively, the compositions can comprise a therapeutically effective amount of from greater than 122.5 g to 700 g of a cross-linked hemoglobin blood substitute in a pharmaceutically acceptable carrier, wherein the cross-linked hemoglobin blood substitute, when tested in a cell culture under normoxic conditions, induces expression of erythropoietin. On the other hand, the compositions can comprise a therapeutically effective volume of less than 0.6 liter of a cross-linked hemoglobin blood substitute in a pharmaceutically acceptable carrier, wherein the cross-linked hemoglobin blood substitute, when tested in a cell culture under normoxic conditions, induces expression of erythropoietin.

Other novel pharmaceutical compositions include a therapeutically effective amount of from 7 g to less than 122.5 g of a cross-linked hemoglobin in a pharmaceutically acceptable carrier, wherein the cross-linked hemoglobin is a hemoglobin that is cross-linked intramolecularly with periodate-oxidized ATP, cross-linked intermolecularly with periodate-oxidized adenosine, and conjugated with reduced glutathione. Alternatively, the composition can comprise a therapeutically effective amount of from greater than 122.5 g to 700 g of a cross-linked hemoglobin in a pharmaceutically acceptable carrier, wherein the cross-linked hemoglobin is a hemoglobin that is cross-linked intramolecularly with periodate-oxidized ATP, cross-linked intermolecularly with periodate-oxidized adenosine, and conjugated with reduced glutathione. In another embodiment, the composition can comprise a therapeutically effective volume of less than 0.6 liter of a cross-linked hemoglobin in a pharmaceutically acceptable carrier, wherein the cross-linked hemoglobin is a hemoglobin that is cross-linked intramolecularly with periodate-oxidized ATP, cross-linked intermolecularly with periodate-oxidized adenosine, and conjugated with reduced glutathione.

In certain embodiments, the cross-linked hemoglobins blood substitutes and cross-linked hemoglobins used in the pharmaceutical compositions of the present invention stabilize HIF-1 alpha expression as tested in a cell culture. In specific embodiments, the cross-linked hemoglobins blood substitutes and cross-linked hemoglobins used in the pharmaceutical compositions of the present invention stabilize 5%, 10%, 20%, 30%, 40%, 50%, 60%, 70%, 80%, 90%, or 100% HIF-1 alpha expression as tested in a cell culture.

In certain other embodiments, the cross-linked hemoglobins blood substitutes and cross-linked hemoglobins used in the pharmaceutical compositions of the present invention down regulate NF-kappa B expression as tested in a cell culture. In specific embodiments, the cross-linked hemoglobins blood substitutes and cross-linked hemoglobins used in the pharmaceutical compositions of the present invention down regulate 5%, 10%, 20%, 30%, 40%, 50%, 60%, 70%, 80%, 90%, or 100% NF-kappa B expression as tested in a cell culture.

In certain embodiments, the cross-linked hemoglobins used in the pharmaceutical compositions of the present invention comprise hemoglobin and periodate-oxidized ATP at a molar ratio of 1:1 to 1:3. In certain embodiments, the cross-linked hemoglobins used in the pharmaceutical compositions of the present invention comprise hemoglobin and periodate-oxidized adenosine at a molar ratio of 1:1 to 1:10. In certain embodiments, the cross-linked hemoglobins used in the pharmaceutical compositions of the present invention comprise hemoglobin and reduced glutathione at a molar ratio of 1:1 to 1:20. In certain embodiments, the cross-linked hemoglobins used in the pharmaceutical compositions of the present invention comprise hemoglobin and periodate-oxidized ATP at a molar ratio of 1:1 to 1:3; hemoglobin and periodate-oxidized adenosine at a molar ratio of 1:1 to 1:10; and hemoglobin and reduced glutathione at a molar ratio of 1:1 to 1:20.

Any cross-linked hemoglobin blood substitutes and cross-linked hemoglobins described in Section 5.3 supra. which exhibit these characteristics can be used in the pharmaceutical compositions of the present invention.

In certain embodiments, the cross-linked hemoglobins used in the pharmaceutical compositions of the present invention is dissolved in a non-electrolytic aqueous solution.

The pharmaceutical compositions can further comprises mannitol and/or electrolytes. Electrolytes that may be used in the pharmaceutical compositions of the present invention include, but are not limited to, sodium, potassium, calcium and magnesium cations, and chloride, bicarbonate, gluconate and sulfate anions.

In specific embodiments, the pharmaceutical compositions of the present invention comprise about 1 g or less, 5 g, 10 g, 15 g, 20 g, 25 g, 30 g, 40 g, 50 g, 60 g, 70 g, 80 g, 90 g, 100 g, 150 g, 200 g, 300 g, 500 g, 1000 g, 2000 g or more blood substitute. In a preferred embodiment, the pharmaceutical compositions of the present invention comprise from about 7 g to less than about 122.5 g of blood substitute. In another preferred embodiment, the pharmaceutical compositions of the present invention comprise from about 122.5 g to about 700 g of blood substitute.

In specific embodiments, the pharmaceutical compositions of the present invention comprise about 0.1 liter or less, 0.2 liter, 0.3 liter, 0.4 liter, 0.5 liter, 0.6 liter, 0.7 liter, 0.8 liter, 0.9 liter, 1.0 liter, 2.0 liter, 5.0 liter, 10.0 liter or more blood substitute. In a preferred embodiment, the pharmaceutical compositions of the present invention comprise from about less than 0.6 liter of blood substitute.

The pharmaceutical compositions of the present invention can be used in the methods of the present invention as well as any other methods, including, but not limited to, treatment of chronic blood loss anemia (e.g., sickle cell anemia).

The pharmaceutical compositions of the present invention can be administered by any methods known to one skilled in the art. Methods of administering the pharmaceutical compositions of the present invention include, but are not limited to, parenteral (e.g., subcutaneous, intramuscular, intraorbital, intracapsular, intraspinal, intrasternal, intravenous, intradermal, intraperitoneal, intraportal), epidural, and mucosal (e.g., intranasal) administration.

In certain embodiments, the pharmaceutical compositions are parenterally administered. Where a pharmaceutical composition is administered parenterally, an ampoule of sterile water or saline can be provided so that the ingredients may be mixed prior to administration. In a specific embodiment, the pharmaceutical compositions of the present invention are administered by infusion. In another specific embodiment, the pharmaceutical compositions of the present invention are administered by injection, preferably by intravenous injection.

The pharmaceutical compositions of the present invention can be formulated into a unit dosage form including, but not limited to, a solid, capsule, tablet, gel, etc. The pharmaceutical compositions of the present invention can also be formulated as a dry lyophilized powder or water free concentrate in a hermetically sealed container such as an ampoule or sachette.

The pharmaceutical compositions of the present invention can be supplied in a kit comprising one or more containers. Each container can comprise the same or a different pharmaceutical composition.

The kits can further comprise a needle or syringe, preferably packaged in sterile form, for injecting the pharmaceutical compositions, and/or a packaged alcohol pad. Instructions are optionally included for administration of the blood substitutes and pharmaceutical compositions of the present invention by a clinician or by the patient.

While the foregoing description and drawings are merely illustrative of the principles of the invention, it will be understood that various additions, modifications and substitutions may be made therein. In particular, it will be clear to those skilled in the art that the present invention may be embodied in other specific forms, structures, arrangements, proportions, and with other elements, materials, and components, without departing from the spirit or essential characteristics thereof. In addition, features described herein may be used singularly or in combination with other features. The presently disclosed embodiments are therefore to be considered in all respects as illustrative and not restrictive, the scope of the invention being indicated by the appended claims, and not limited to the foregoing description.

6. EXAMPLES

The following examples are provided by way of describing specific embodiments of the present invention without intending to limit the scope of the present invention in any way.

6.1. Example One—Increase of Hematocrit In Vivo With Treatment With Hemoglobin-ATP-Adenosine-GSH-Based Blood Substitute in Primates Under Life Threatening Anemia

6.1.1. Methods

Experiments were conducted in four groups of six Coebus monkeys each, subjected to blood removal equal to one-third (33%) and two-third (66%) of calculated blood volume, followed by the isovolemic infusion of 10 g per dL hemoglobin-ATP-adenosine-GSH blood substitute, according to a method previously reported in scientific literature (Feola et al. (1988) Circulatory Shock 25:275-290).

In this experiment homologous plasma was used in place of the blood substitute, to serve as control. Healthy male monkeys, weighting 4 to 5 kg, were sedated with ketamine HCl 12.5 mg/kg, intramuscularly. Sterile 16-gauge Teflon catheters were inserted precutaneously into femoral artery and one femoral vein. Heparin was not administered. The animals were allowed to breathe room air spontaneously. After the preparation was stabilized, monkeys were assigned to one of the following treatment groups: (I). one third (33%) of calculated total blood volume was removed from femoral artery and replaced with an equal volume of hemoglobin-ATP-adenosine-GSH based blood substitute (approximately 2.3 g per kg body weight) infused through the venous line; (II). two-third (66%) of calculated total blood volume was removed from femoral artery and replaced with an equal volume of hemoglobin-ATP-adenosine-GSH based blood substitute (approximately 4.6 g per kg body weight) infused through the venous line; (III). one-third (33%) of calculated total blood volume was removed from femoral artery and replaced with an equal volume of homologous plasma infused through the venous line; and (IV). two-third (66%) of calculated total blood volume was removed from femoral artery and replaced with an equal volume of homologous plasma infused through the venous line.

Blood samples were taken at baseline, after removal of blood and at 1, 2, 4, 5, 7, 9, 11, 14, 16, 18, 20, 22 and 24 days following infusion of hemoglobin-ATP-adenosine-GSH-based blood substitute and homologous plasma, and tested for hematocrit, which is the most powerful indicator of erythropoiesis in blood samples containing plasma free hemoglobin. The hematocrit is the ratio of the volume of packed red cells to the volume of whole blood, expressed as a percentage. The hematocrit was measured using heparinized micro-hematocrit capillary tubes (Fisher Scientific, Houston, Tex.) and micro-hematocrit centrifuge (Damon ICE Division, Needham, Mass.).

6.1.2. Results

All animals in group I, II and III survived the treatment, however in group IV, one (16%) animal died within 24 hours.

As seen in FIG. 1 following the removal of one-third and two-thirds of calculated total blood volume, the hematocrit falls to approximately 30% (Hb was approximately 9 g per dL) and 13% (hemoglobin was approximately 4.5 g per dL), respectively. The administration of hemoglobin-ATP-adenosine-GSH-based blood substitute brought the hematocrit back to the baseline value after approximately 3.5 days following replacement of one-third of calculated total blood volume (Group I), and approximately 8.5 days following replacement of two-thirds of the calculated total blood volume (Group II). On the contrary, animals treated with homologous plasma were unable to quickly normalize hematocrit. In group III, which received 33% replacement transfusion with plasma, the hematocrit came back to normal after approximately 10 days, and in group IV, which received 66% replacement transfusion, the hematocrit reached the baseline value after approximately 24 days.

While in the blood substitute group (II), which received 66% replacement therapy, the hematocrit doubled in less than 3 days, in group IV, treated with homologous plasma, in surviving animals, the hematocrit doubled in approximately 10 days.

6.1.3. Conclusions

The administration of hemoglobin-ATP-adenosine-GSH-based blood substitute resulted in an extremely quick restoration of the red blood cell mass to a normal value, even after life threatening (66%) blood loss. This blood substitute accelerated more than twice the natural erythropoietic response to acute blood loss anemia. Assuming that circulatory half-life of this blood substitute is approximately 24 hours, this product acted not simply as an oxygen carrier in initial resuscitation phase, but also as an effective stimulator of erythropoietic responses.

The reported hematocrit doubling time in patients with life threatening anemia treated experimentally with other blood substitute was between 10 and 24 days, even after the concurrent treatment with massive doses of recombinant EPO (Lanzinger et al. (2005) Can J Anaesth 52(4):369-373; Gannon et al. (2002) 30(8):1893-1895; Allison et al. (2004) 97(12):1257-1258).

Since in normal situations erythropoiesis (from Pluripotent Stem Cell to RBC) should occur in 5 days, the results obtained with the currently tested blood substitute products (supported by EPO) are clinically unacceptable, showing direct toxic effects of these hemoglobins on the bone marrow cells.

On the contrary, less than 3 days doubling time of hematocrit following treatment with hemoglobin-ATP-adenosine-GSH-based blood substitute alone, suggests that this blood substitute product has true, unique and direct erythropoietic potential.

6.2. Example Two—Increase of Hematocrit In Vivo With Treatment With Hemoglobin-ATP-Adenosine-GSH-Based Blood Substitute in Rabbits Under Life Threatening Anemia 6.2.1. Methods Twelve New Zealand rabbits of 4.0 Kg body weight had sterile cannulae inserted under local anesthesia with 1% lidocaine into the central artery of one ear and the marglobal vein of the other ear, according to methods previously reported in scientific literature (Feola et al. (1988) Surg Gynecol Obstet 166:211-222; Simoni et al. (1990) Biomat Art Cells Art Org 18(2): 189-202).

Following instrumentation, rabbits were subjected for removal of one-third (33%) of calculated total blood volume, followed by the removal of another one-third (33%) after 15 minutes. The experimental rabbits (n=6) received an infusion of hemoglobin-ATP-adenosine-GSH-based blood substitute in the same volume as the total blood loss (approximately 4.6 g per kg body weight). Another 6 animals after bleeding received no treatment. Within one hour all of these animals died. All experimental groups of animals that received an infusion of blood substitute survived.

Blood samples were taken at baseline, after bleeding and at 1, 2, 4, 7, 9, and 14 days following infusion of hemoglobin-ATP-adenosine-GSH-based blood substitute. Blood samples were tested for hematocrit as in Example One.

6.2.2. Results

Conclusions

Figure 2:
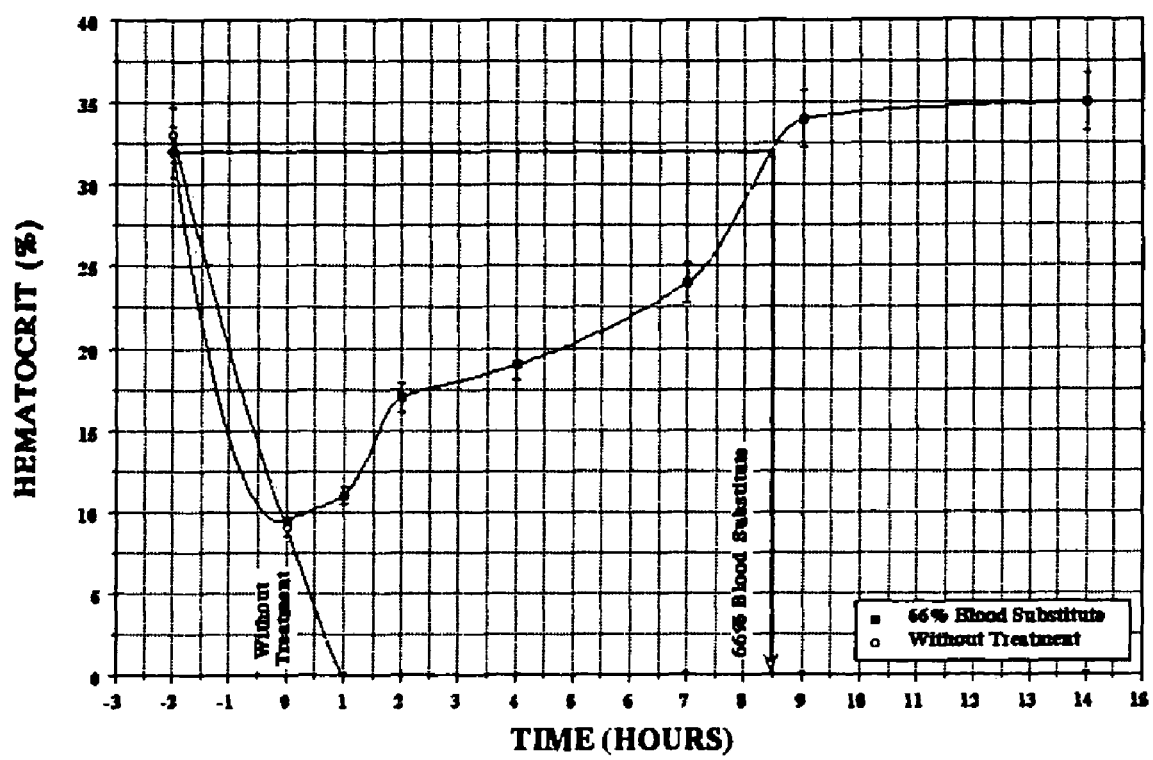
FIG. 2 shows the hematocrit (in percent) of rabbits suffering from 66% of the total blood loss, treated with hemoglobin-ATP-adenosine-GSH-based blood substitute or without treatment.

As seen in FIG. 2 following the removal of two-thirds of calculated total blood volume, the hematocrit falls to approximately 9.5% (hemoglobin was approximately 4.0 g per dL). The administration of hemoglobin-ATP-adenosine-GSH-based blood substitute reconstituted their baseline hematocrit in approximately 8.5 days. Also in rabbits, the administration of hemoglobin-ATP-adenosine-GSH-based blood substitute resulted in an extremely quick restoration of the red blood cell mass to a normal value, even after life threatening (66%) blood loss. The hematocrit doubling time was approximately 3 days. Also in rabbits, this blood substitute product acted not simply as an oxygen carrier in initial resuscitation phase, but also as an effective stimulator of erythropoiesis.

6.3. Example Three—Hemodynamics and Tissue Oxygenation of Normotensive Rats With Life Threatening Anemia After Resuscitation With Hemoglobin-ATP-Adenosine-GSH-Based Blood Substitute 6.3.1. Methods Ten male normotensive Sprague-Dawley rats (Charles River, Kingston, N.Y.) weighting 350-450 gm were anesthetized intraperitonealy with 30 mg/kg body weight of sodium pentobarbital and subjected to an aseptic microsurgical procedure, according to injection of sodium pentobarbital and subjected to an aseptic microsurgical procedure, according to a method previously reported in scientific literature (Simoni et al. (1996) ASAIO J 42(5):M773-782).

To access hemodynamic values and collect the reference sample, the right and left femoral artery, left femoral vein, and external jugular vein were surgically exposed and cannulated with polyethylene catheters (model PE-50, Becton Dickinson and Co., Parsippany, N.J.). Continuous measurement of arterial blood pressure was performed through a catheter located in the right femoral artery and connected with a disposable, small volume blood pressure transducer (Ohmeda, Pte, Ltd, Singapore). To measure cardiac output (CO) a thermostat microprobe (model IF, ⅓ mm in O.D.; Columbus Instruments, Columbus, Ohio) was advanced through the carotid artery into the ascending aorta, while the injection of 100 μL of saline solution, at room temperature, was made into the right atrium via a catheter placed in the external jugular vein. To measure tissue oxygenation (tpO$_2$), a DO-166 oxygen microprobe (Lazar Research Laboratories, Inc., Los Angeles, Calif.) was surgically inserted into the biceps femori muscle (right leg). The blood temperature was maintained at 37±0.1° C. with a heating pad throughout the entire experiment. All animals were allowed to breathe spontaneously.

studied during a post treatment period of 90 min. At the end of experiment, the rats were killed by intravenous administration of sodium pentobarbital.

6.3.2. Results

Figure 3:
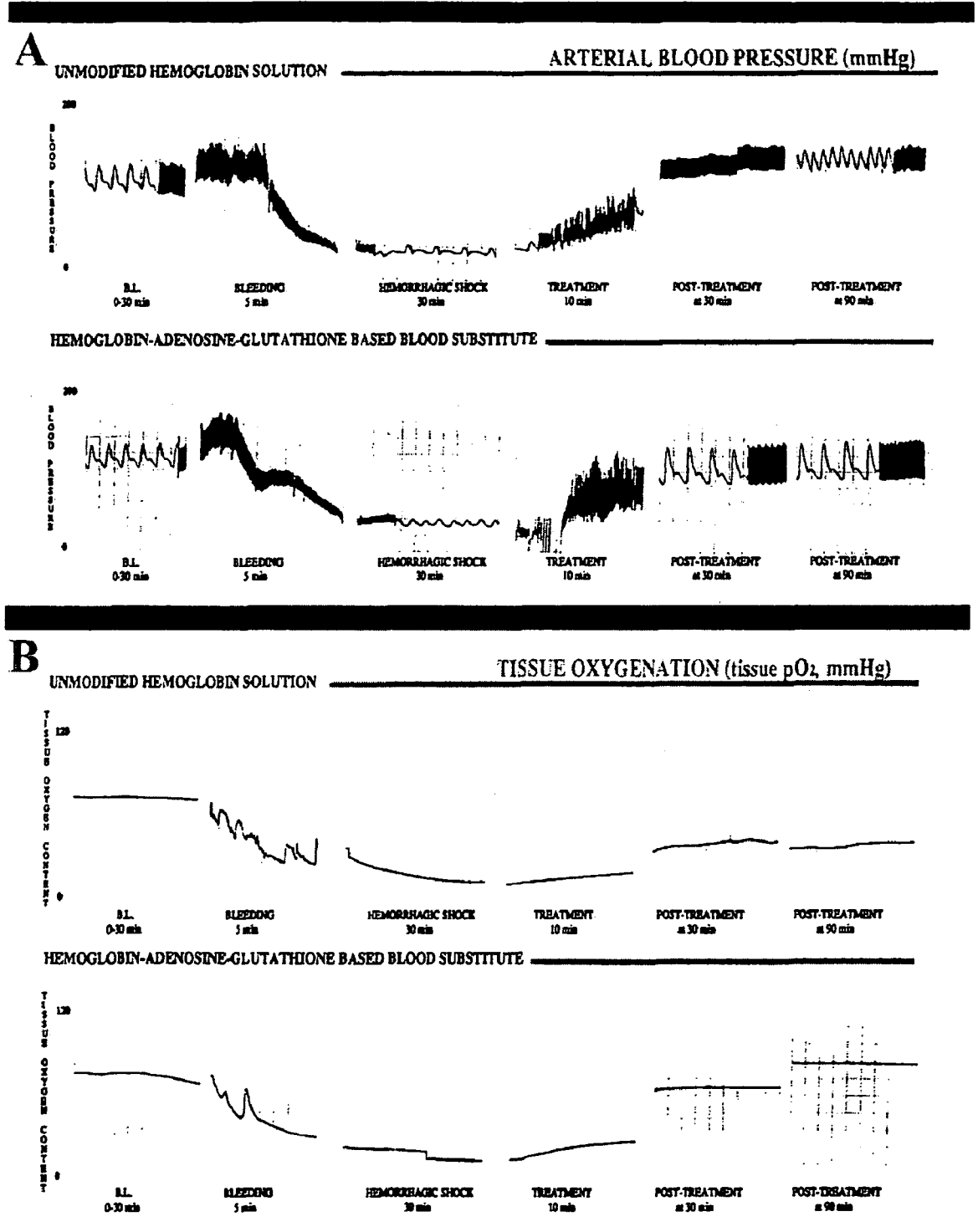
FIG. 3 is a graphical representation of blood pressure and tissue oxygenation ($pO_2$) of rats suffering from 40% of the total blood loss treated with hemoglobin-ATP-adenosine-GSH-based blood substitute.

The results, summarized below (TAB. 1) and in FIG. 3, show increased TPR and decreased CI, MAP and tissue pO$_2$, after blood removal, followed by immediate reduction of TPR to normal and quick normalization of CI, MAP and tissue pO$_2$. Moreover, vasodilation and better tissue oxygenation were seen in the entire post-treatment period.

TABLE 1

HEMODYNAMIC PROFILES AFTER TREATMENT WITH
HEMOGLOBIN-ATP-ADENOSINE-GSH-BASED BLOOD SUBSTITUTE

|  | BASELINE | HEMORRHAGE | 30 MIN POST-TREATMENT | 90 MIN POST-TREATMENT |
| --- | --- | --- | --- | --- |
| CI—Cardiac Index (ml/min/100 g BW) | 34 ± 3 | 12 ± 2 ($p < 0.001$) | 34 ± 3 N.S. | 33 ± 4 N.S. |
| Stroke Volume Index (ml/beat/100 g BW) | 0.098 ± 0.01 | 0.040 ± 0.01 ($p < 0.001$) | 0.121 ± 0.01 ($p < 0.001$) | 0.089 ± 0.01 N.S. |
| MAP—Mean Arterial Pressure (mmHg) | 118 ± 12 | 40 ± 5 ($p < 0.001$) | 116 ± 13 N.S. | 119 ± 7 N.S. |
| PP—Pulse Pressure (mmHg) | 28 ± 2 | 22 ± 3 ($p < 0.01$) | 38 ± 3 ($p < 0.001$) | 30 ± 3 ($p < 0.05$) |
| TPR (dyn/sec/cm$^{-5}$) × 10$^3$ | 84 ± 12 | 90 ± 12 ($p < 0.05$) | 77 ± 7 ($p < 0.05$) | 78 ± 10 ($p < 0.1$) |
| Tissue pO$_2$ (ml O$_2$/min) | 80 ± 9 | 20 ± 3 ($p < 0.001$) | 72 ± 4 N.S. | 93 ± 12 ($p < 0.05$) |
| NUMBERS: | MEAN | ±SD | | |
| SIGNIFICANCE: | (P) | DIFFERENCE | FROM | BASELINE |

Hemodynamic parameters, including cardiac output (CO; in ml/min; cardiac index (CI) in ml/min/100 g body weight), stroke volume (SV; in ml/beat/100 g body weight), mean arterial pressure (MAP; in mmHg), pulse pressure (PP; in mmHg), heart rate (HR; in beats/min), total peripheral resistance (TPR; in (dyn/sec/cm$^{-5}$)×10$^3$), and blood temperature were recorded by using a fully automatic, Cardiomax Circulatory System Computer (Columbus Instruments, Columbus, Ohio). Continuous recording of tissue oxygenation was achieved by connecting the interface of the DO-166 probe with Microcomputer (pH-version 6071, Lazar Research Laboratories) and chart recorder of the Cardiomax Circulatory System Computer.

The arterial blood oxygen content (in ml O$_2$ in 100 ml of blood) was calculated by multiplying the amount of hemoglobin (in grams) by the known oxygen saturation and by 1.36 (the amount of oxygen a fully saturated gram of hemoglobin to carry). Blood oxygen transport (in ml O$_2$/min) was calculated by multiplying the CO (in L/min) by the arterial blood oxygen transport (in ml per 100 ml of blood) by adjusts factor of 10.

After completing the surgical preparation and calibration of the Cardiomax system, 30 min were allocated for stabilization of hemodynamics and tissue oxygen content parameters. Hemorrhagic shock was induced by withdrawal of arterial blood in a volume corresponding to 40% of total blood volume (calculated for each rat as equal to 7% of body weight in kilograms) or 2.8 g per kg body weight. The withdrawal of blood was completed in 5 min. Hemorrhagic shock was continued for 30 min. Consequently, the rats were treated with hemoglobin-ATP-adenosine-GSH-based blood substitute in the same volume as the total blood loss. The treatment was completed in approximately 10 min. All the rats were then 6.3.3. Conclusions This experiment showed that hemorrhagic shock characterized by approximately a 66% drop in cardiac index, approximately 67% drop in mean arterial pressure with significant increase in TPR, and approximately 78% reduction in tissue oxygenation, can be successfully treated with hemoglobin-ATP-adenosine-GSH-based blood substitute. The vasodilatory activity, and the reduction of vasoconstriction that followed hemorrhage can be primarily linked with adenosine, which possesses vasodilatory and anti-inflammatory properties, and is used in our technology (U.S. Pat. No. 5,439,882 to Feola, Simoni and Canizaro) as an intermolecular cross-linking reagent and hemoglobin surface modifier. This experiment also proved that the treatment hemoglobin-ATP-adenosine-GSH-based blood substitute improved tissue oxygenation by maximizing tissue/organ perfusion.

Proper oxygen delivery to ischemic organs is the essential factor in the regulatory approval of these agents as blood substitute. In vivo maximization of oxygen delivery to the ischemic tissues and organs did not block the erythropoietic responses, as shown in FIG. 1, FIG. 2, FIG. 3, FIG. 4, FIG. 5, and FIGS. 6A & B.

6.4. Example Four—Erythropoietic Effect of Hemoglobin-ATP-Adenosine-GSH-Based Blood Substitute Used in the Treatment of Sickle Cell Anemia Patients 6.4.1. Methods Hemoglobin-ATP-adenosine-GSH-based blood substitute was tested in humans, as previously reported in scientific literature (Feola et al. (1992) Surg Gynecol Obstet 174(5): 379-386). A group of nine patients was treated at the Center for Sickle Cell Anemia in Kinshasa. There were 5 males and 4 females, 4-13 years of age. Five of the children presented severe anemia, with blood hemoglobin levels of 5 g per dL or less. Four of the children had a lesser degree of anemia, with hemoglobin level approximately 8 g per dL, but were suffering from a "sickle cell crisis," i.e., acute microvascular blockage in the hands and feet (2 patients), in the left lung (1 patient), and in the spleen (1 patient). The patients presented pain, fever and generalized malaise and weakness.

Hemoglobin-ATP-adenosine-GSH-based blood substitute was injected intravenously in a volume corresponding to 25% of the total blood volume, (calculated for each patient as 7% of body weight in kilograms), approximately 1.75 g per kg body weight. One patient with severe anemia, initial hemoglobin 3.5 g per dL, received two transfusions on two consecutive days.

The vital signs, temperature, pulse, respiration, and blood pressure, were taken every 15 minutes during the administration of the blood substitute and for 2 hours after. Urinary output was measured for a two-hour period before and two-hour period after blood substitute administration. The urine was tested for the presence of hemoglobin.

Blood samples were taken before, soon after blood substitute administration, two hours thereafter, and daily for 5 days. The patient blood was tested for plasma free hemoglobin, total hemoglobin and for reticulocytes.

A small volume of EDTA plasma was stored in $-20°$ C. and later subject for measurement of erythropoietin level. EPO was detected with EPO-Trac $^{125}$I RIA Kit (INCSTAR Corp. now Dia Sorin S.p.A., Sallugi, Italy). The INCSTAR EPO-Trac $^{125}$I RIA procedure is a competitive binding radioimmunoassay, which utilizes recombinant human erythropoietin for both tracer and standards. With this assay the minimum detectable concentration of EPO is 5.5 mU/mL. The interference study, conducted by the Company, demonstrated that severe hemolysis (hemoglobin approximately 4 g per dL) did not appear to interfere with the EPO-Trac RIA. The results were expressed in mU/mL of plasma.

6.4.2. Results

None of the patients developed allergic reactions, and all health generally improved. The fever abated, the pulse become less rapid, the blood pressure remained stable with an increase in pulse pressure, indicative of vasodilation (TAB. 2).

TABLE 2

| Blood Pressure (mmHg) | Before Treatment | After Treatment | Significance |
|---|---|---|---|
| Systolic | 108 ± 10 | 107 ± 8 | N.S. |
| Diastolic | 65 ± 6 | 58 ± 6 | P < 0.02 |

Figure 4:
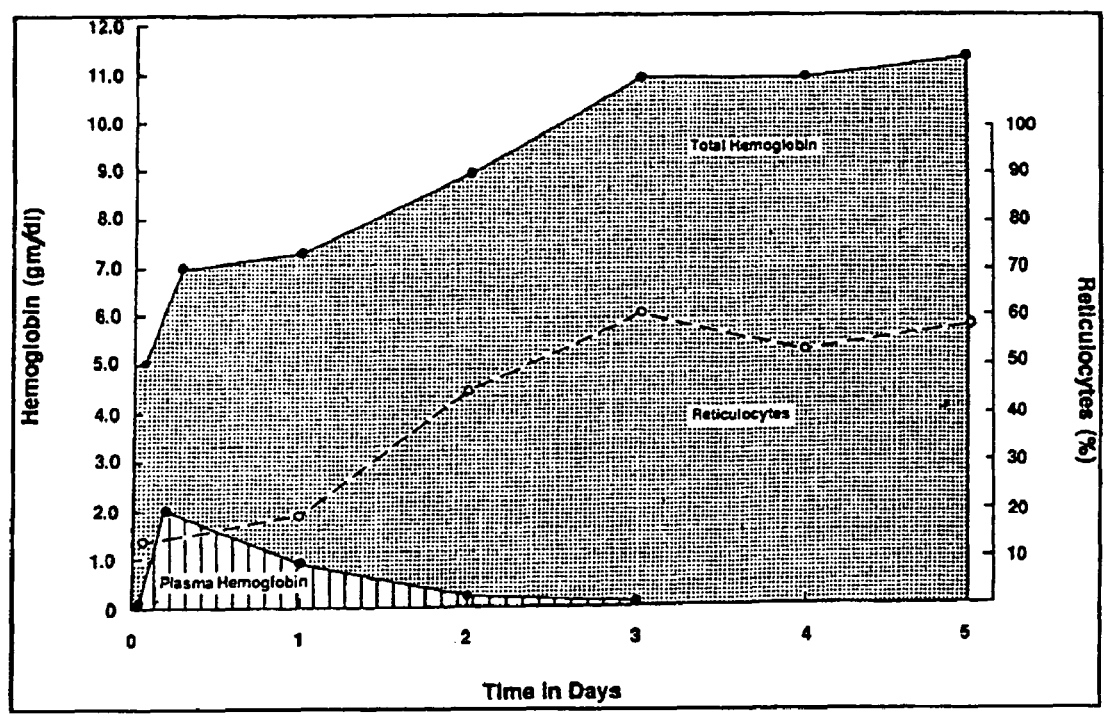
FIG. 4 shows summary data including total hemoglobin (in g per dL), plasma hemoglobin (in gm/dL) and reticulocyte count (in percent) obtained from a sickle cell anemia patient treated with hemoglobin-ATP-adenosine-GSH-based blood substitute in a dose of approximately 1.75 g per kg body weight (25% of calculated total blood volume).

As seen in FIG. 4, hemoglobin-ATP-adenosine-GSH-based blood substitute progressively improved the total hemoglobin over the period of 5 days from a mean value for the entire group of approximately 6.3±2.0 to approximately 10.9±1.3 g per dL (p<0.001), with doubling time of approximately 7 days.

As seen in FIG. 4, an increase in the total hemoglobin was associated with a significant increase in reticulocytes from approximately 3.7±3.1 to approximately 44.2±7.2 per cent (p<0.001).

Figure 5:
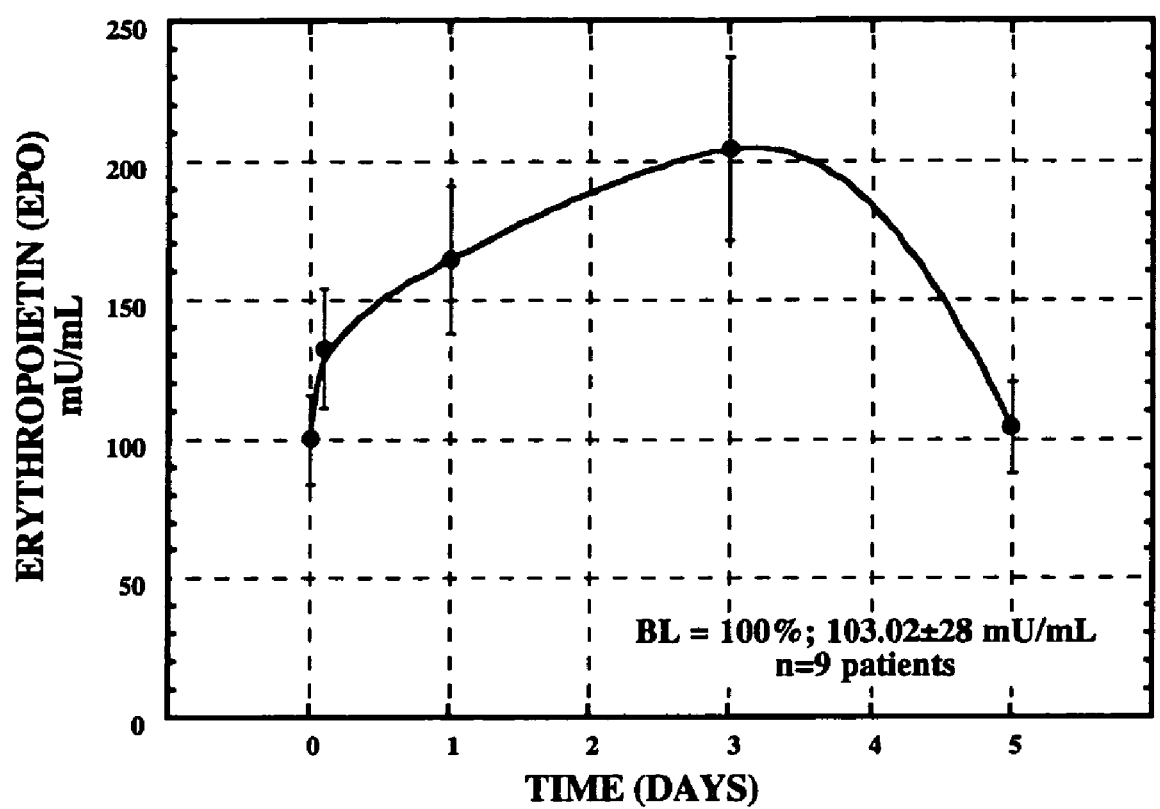
FIG. 5 shows blood level of EPO in sickle anemia patients treated with hemoglobin-ATP-adenosine-GSH-based blood substitute in a dose of approximately 1.75 g per kg body weight (25% of calculated total blood volume).

As seen in FIG. 5, the treatment with hemoglobin-ATP-adenosine-GSH-based blood substitute significantly increased the circulating EPO level. After 1 day, EPO levels rose approximately 1.6 times, reaching the maximum concentration of approximately 210 mU/mL at day 3. At day 5, the level of EPO was still slightly higher than at baseline.

The treatment with hemoglobin-ATP-adenosine-GSH-based blood substitute resulted in an extreme restoration of the total hemoglobin to a normal value. This blood substitute accelerated the synthesis of EPO, which results in a massive production of reticulocytes.

This suggests that the hemoglobin-ATP-adenosine-GSH-based blood substitute not only provided an immediate substitute for RBCs, but stimulated the synthesis of EPO which accelerated the production of new RBCs. This stimulation was solely documented for 5 days.

6.4.3. Conclusions

In conclusion, the administration of hemoglobin-ATP-adenosine-glutathione-based blood substitute in significant volumes to humans suffering from life threatening anemia produced no toxic or allergic reactions, improved their general condition and stimulated patients' erythropoietic responses.

6.5. Example Five—The Effect of Hemoglobin-ATP-Adenosine-GSH-Based Blood Substitute on Pro-Erythropoietic Factors; HIF-1 Alpha Stabilization and Production of EPO in Normoxia and Hypoxia Using Human Astrocytes as a Model 6.5.1. Methods To evaluate whether the hemoglobin-ATP-adenosine-GSH-based blood substitute acted as a stabilizer of HIF-1 alpha, which is known as an inducer of the EPO gene, we evaluated the effect of this blood substitute on human astrocytes that are capable of EPO production.

Characteristically, EPO an essential stimulator of erythropoiesis, is produced by the fetal liver and adult kidney. Recently, a new site of EPO production has been found: central nervous system. In the central nervous system, astrocytes are the main producers of EPO in response to hypoxia/ischemia (Siren A L, Knerlich F, Poser W, Gleiter C H, Bruck W, Ehrenreich H: Erythropoietin and erythropoietin receptor in human ischemic/hypoxic brain. Acta Neuropathol (Berl) 101 (3):271-276, 2001; Sasaki R: Pleiotropic functions of erythropoietin. Int Med 42(2):142-149, 2003).

In astrocytes, HIF-1 alpha regulates EPO expression. EPO appears to play a neuroprotective role to shield neurons from hypoxic/ischemic stress. EPO induced neuroprotection is based on phosphorylation of the proapoptotic Bcl family member Bad. Since the EPO receptor is expressed in neurons, EPO by activating the neuronal EPO receptor may inhibit hypoxia-induced apoptosis in neurons (Variano M, Dello Russo C, Pozzoli G, Battagia A, Scambia G, Tringali G, Aloe-Spiriti M A, Preziosi P, Navarra P: Erythropoietin exerts anti-apoptotic effects on rat microglial cells in vitro. Eur J Neurosci 16(4):684-692, 2002).

Since the principal function of EPO in erythropoiesis is to rescue erythroid progenitors from apoptosis (Socolovsky et al. (1999) Cell 98(2):181-91; Dolznig et al. (2002) Curr Biol 12(13): 1076-1085), we thought that the astrocyte model would be the best human cellular system to study the effects of blood substitute on HIF-1 alpha's fate and EPO synthesis.

Normoxia

The initial culture of normal human astrocytes, $2^{nd}$ passage, was obtained from Clonetics (Bio-Wittaker, A Cambrex Co, San Diego, Calif.). Cells were cultured in 75 cm$^2$ tissue culture flasks (Corning Glass Works, Corning, N.Y.) with AGM BulletKit medium (Clonetics) in a humidified atmosphere of 5% $CO_2$ and temperature of 37° C., until they reached confluence (approximately 50,000 cells/cm$^2$). Astrocytes were then subcultured in 6-well cell culture plates (Corning) and glass cover slips. Cell passage was carried out using a trypsin reagent pack (Clonetics). During the transfer, astrocytes were trypsinized no longer than 5 min. All experiments were performed using fourth to sixth cell passage. The astrocytes had previously been tested negative for HIV, hepatitis, mycoplasma, bacteria, yeast, fungi; and tested positive for GFAP and stained negative for CD68 and CNPase (Clonetics Certificate of Analysis).

Then the confluent astrocytes were incubated for approximately 18 hours with a medium supplemented with hemoglobin-ATP-adenosine-GSH-based blood substitute in a final concentration of 0.1, 1.0, and 1.75 g per dL. Positive control astrocytes were incubated with a medium supplemented with unmodified hemoglobin in a final concentration of 0.1, 1.0 and 1.75 g per dL. Negative control astrocytes were cultured in the absence of hemoglobin solutions that were replaced by FBS.

All experiments were conducted in an atmosphere of 95% air, representing normoxic conditions. After treatment, the cells were subjected to evaluation by various biochemical and molecular biology methods.

The impact of the hemoglobin-ATP-adenosine-GSH-based blood substitute on HIF 1 alpha stabilization and its ability to induce the human EPO gene in normoxic conditions were measured in cellular nuclear extracts using a high-throughput TransAM ELISA based assay (Active Motif, Carlsbad, Calif.). In this assay, a 96-well plate was immobilized with an oligonucleotide containing a hypoxia responsive element (5'-TACGTGCT-3') from a human EPO gene. Nuclear extracts were obtained from living astrocytes using Nonident P-40 and lysis buffer supplemented with DTT and a protease inhibitor cocktail (Active Motif). Nuclear extracts were subjected for the detection of HIF-1 alpha. HIF-1 alpha present in the nuclear extracts bound to the human EPO gene and was accessible to primary antibodies. Then, the primary antibodies were recognized by secondary, HRP-conjugated antibodies, which provided a sensitive colorimetric readout. The reaction was read at 450 run using a 3550-UV microplate reader (BioRad). Results were expressed in OD at 450 nm per 2.5 µg of nuclear extract. The COS-7 nuclear extract provided by the manufacturer was used as a positive control for HIF-1 alpha activation and binding to the EPO gene.

The influence of the hemoglobin-ATP-adenosine-GSH-based blood substitute on EPO synthesis was assessed in the cell culture supernatant using highly specific Quantikine In Vitro Diagnostic Human Erythropoietin ELISA (R&D Systems Inc., Minneapolis, Minn.). This assay is based on a double-antibody sandwich method. Microplate wells, pre-coated with monoclonal antibody specific for human EPO were incubated with cell culture supernatants or human EPO standards. After incubation and washing, wells were incubated with an anti-EPO polyclonal antibody conjugated with HRP. During the second incubation, the antibody-enzyme conjugate binds to the immobilized EPO. After washing, a chromogen is added to form a blue colored complex. The amount of color generated is directly proportional to the amount of EPO in the samples or standard. The results were expressed in mU/mL. The minimum detectable EPO dose with this assay was less than 0.6 mU/mL.

Hypoxia

Hypoxic conditions (1.5% $O_2$, 93.5% $N_2$, and 5% $CO_2$) were achieved in a humidified variable aerobic workstation. Before experimentation, media was pre-equilibrated overnight at a 1.5% oxygen level.

The confluent astrocytes, cultured as above, were exposed to hypoxia (1.5% $O_2$) for approximately 18 hours in the presence of pre-equilibrated medium supplemented with the hemoglobin-ATP-adenosine-GSH-based blood substitute in a final concentration of 0.1, 1.0, and 1.75 g per dL. Positive control astrocytes were incubated with pre-equilibrated medium supplemented with unmodified hemoglobin in a final concentration of 0.1, 1.0 and 1.75 g per dL. Negative control astrocytes were cultured in the absence of hemoglobin solutions that were replaced by FBS.

All procedures were carried out in the dark in an atmosphere of 1.5% $O_2$, 95.5% $N_2$ and 5% $CO_2$, representing hypoxic conditions. After exposure, the cells were evaluated for:

1). effects of hemoglobin-ATP-adenosine-GSH-based blood substitute on HIF-1 alpha stabilization and its ability to induce the human EPO gene, performed by the TransAM ELISA method, as described above, and 2). influences of the hemoglobin-ATP-adenosine-GSH-based blood substitute on EPO synthesis in hypoxia which was assessed with Quantikine IVD human EPO ELISA, as described above.

6.5.2. Results

The effect of the hemoglobin-ATP-adenosine-GSH-based blood substitute and unmodified hemoglobin solution on pro-erythropoietic factors; HIF-1 alpha and EPO are presented in TAB. 3 and 4 and FIGS. 6 and 7.

TAB. 3 represents the effects of the hemoglobin-ATP-adenosine-GSH-based-blood substitute and unmodified hemoglobin solution on HIF-1 alpha stability and its binding to the EPO gene under hypoxic and normoxic conditions.

TABLE 3

| HIF-1 alpha (O.D. 450 nm/ 2.5 µg of nuclear extract/well) | HYPOXIA | | | NORMOXIA | | | |
|---|---|---|---|---|---|---|---|
| | M ± SD | Significance Cont. vs. Exp | Significance Between Exp Groups | M ± SD | Significance Cont. vs. Exp | Significance Between Exp Groups | Significance HYP. vs. NORM |
| CONTROL | 0.233 ± 0.05 | — | | 0.063 ± 0.01 | | | P < 0.01 |
| Unmod. Hb 0.1 g/dL | 0.198 ± 0.04 | N.S. | — | 0.094 ± 0.02 | P < 0.01 | — | P < 0.01 |
| Unmod. Hb 1.0 g/dL | 0.154 ± 0.03 | P < 0.01 | — | 0.071 ± 0.01 | N.S. | — | P < 0.01 |
| Unmod. Hb 1.75 g/dL | 0.149 ± 0.02 | P < 0.01 | — | 0.066 ± 0.01 | N.S. | — | P < 0.01 |
| Blood Subst. 0.1 g/dL | 0.226 ± 0.02 | N.S. | N.S. | 0.139 ± 0.02 | P < 0.01 | P < 0.01 | P < 0.01 |
| Blood Subst. 1.0 g/dL | 0.264 ± 0.04 | P < 0.01 | P < 0.01 | 0.146 ± 0.03 | P < 0.01 | P < 0.01 | P < 0.01 |

TABLE 3-continued

| HIF-1 alpha (O.D. 450 nm/ 2.5 µg of nuclear extract/well) | HYPOXIA | | | NORMOXIA | | | |
|---|---|---|---|---|---|---|---|
| | M ± SD | Significance Cont. vs. Exp | Significance Between Exp Groups | M ± SD | Significance Cont. vs. Exp | Significance Between Exp Groups | Significance HYP. vs. NORM |
| Blood Subst. 1.75 g/dL | 0.391 ± 0.07 | P < 0.01 | P < 0.01 | 0.234 ± 0.03 | P < 0.01 | P < 0.01 | P < 0.01 |
| ASSAY CONTROL | 0.787 ± 0.02 | | | 0.679 ± 0.02 | N.S. | | |

TAB. 4 represents the effects of the hemoglobin-ATP-adenosine-GSH-based-blood substitute and unmodified hemoglobin solution on EPO production under hypoxic and normoxic conditions.

and hypoxic conditions. The erythropoietic effect was seen at any tested concentration. The hemoglobin-ATP-adenosine-GSH-based blood substitute acted as an effective pro-erythropoietic factor.

TABLE 4

| EPO (mU/mL) | HYPOXIA | | | NORMOXIA | | | |
|---|---|---|---|---|---|---|---|
| | M ± SD | Significance Cont. vs. Exp | Significance Between Exp Groups | M ± SD | Significance Cont. vs. Exp | Significance Between Exp Groups | Significance HYP. vs. NORM |
| CONTROL | 0.233 ± 0.56 | — | | 0.29 ± 0.50 | — | | P < 0.001 |
| Unmod. Hb 0.1 g/dL | 3.05 ± 2.56 | N.S. | — | 2.63 ± 1.33 | P < 0.01 | — | N.S. |
| Unmod. Hb 1.0 g/dL | 2.35 ± 1.62 | N.S. | — | 3.88 ± 1.41 | P < 0.01 | — | N.S. |
| Unmod. Hb 1.75 g/dL | 1.02 ± 0.26 | P < 0.001 | — | 1.96 ± 1.53 | N.S. | — | N.S. |
| Blood Subst. 0.1 g/dL | 3.96 ± 2.68 | N.S. | N.S. | 3.19 ± 1.58 | P < 0.05 | N.S. | N.S. |
| Blood Subst. 1.0 g/dL | 23.00 ± 8.21 | P < 0.001 | P < 0.001 | 6.11 ± 1.86 | P < 0.001 | P < 0.001 | P < 0.001 |
| Blood Subst. 1.75 g/dL | 57.27 ± 27.6 | P < 0.001 | P < 0.001 | 17.67 ± 4.00 | P < 0.001 | P < 0.001 | P < 0.001 |

6.5.3. Conclusions

This study has shown that HIF-1 alpha can be found in the nuclear extracts of astrocytes under hypoxic and normoxic conditions. Moreover, this study has shown that tested hemoglobin solutions have a different impact on HIF-1 alpha stabilization, nuclear translocation and binding to the EPO gene in an hypoxic and normoxic environment.

As seen in FIG. 6A and TAB. 3, the unmodified hemoglobin solutions increased the cytoplasmic degradation of HIF-1 alpha and significantly decreased (in higher doses) its binding activity to the EPO gene, especially in hypoxia. The unmodified hemoglobin solution did not stabilize HIF-1 alpha under normoxic or hypoxic conditions.

On the contrary, the hemoglobin-ATP-adenosine-GSH-based blood substitute increased the induction of HIF-1 alpha under both oxygen conditions. This blood substitute in a dose dependent manner stabilized HIF-1 alpha and increased its binding to the EPO gene. This blood substitute at any tested concentration was able to stabilize HIF-1 alpha under normoxia and hypoxia. The product was the most effective at dose of 1.0-1.75 g per dL. Such a transcriptional effect suggests the acceleration of erythropoietic responses.

In fact, as seen in FIG. 6B and TAB. 4, this blood substitute effectively increased the production of EPO under normoxic and hypoxic conditions. The erythropoietic effect was seen at any tested concentration. The hemoglobin-ATP-adenosine-GSH-based blood substitute acted as an effective pro-erythropoietic factor.

The unmodified hemoglobin blocked the synthesis of EPO, suggesting the inhibition of erythropoiesis. This effect was seen more effective at higher hemoglobin concentrations.

6.6. Example Six—The Effect of Hemoglobin-ATP-Adenosine-GSH-Based Blood Substitute on Anti-Erythropoietic Factors; NF-Kappa B, TNF-Alpha and TGF-Beta 1 and Apoptosis in Normoxia and Hypoxia Using Human Astrocytes and a Model

6.6.1. Methods

Since human astrocytes are known to produce inflammatory cytokines, such as TNF, IL-1, IL-6, TGF-beta 1, which act as anti-erythropoietic agents (Hellwing-Burgel et al. (1999) Am Soc Hematol 94:1561-1567; Linch D C (1989) Schweiz Med Wochenschr 119(39): 1327-1328; Trey et al. (1995) Crit Rev Oncol Hematol 21:1-8; Yuen et al. (2005) ASAIO J 51(3):236-241), we choose this human cellular model to study the anti-inflammatory potency of the blood substitute and its impact on HIF-1 alpha stability and EPO induction (Van Wagoner et al. (1999) J Neurosci 19(13): 5236-5244; Oh et al. (1999) J Neurovirol 5(1):82-94; Flanders et al. (1998) Prog Neurobiol 54(1):71-85).

As stated in the background section, unmodified and modified hemoglobin solutions have a strong pro-apoptotic effect (Meguro et al. (2001) J Neurochem 77(4):1128-1135; Simoni et al. (2002) ASAIO J 48(2):193; Goldman et al. (1998) Am J Physiol 275(3 Pt2):H 1046-53); D'Agnillo et al. (2001) Blood 98(12):3315-3323; Mohara et al. (2005) ASAIO J 51(3):288-295).

Since the principal function of EPO is to protect pro-erythroblasts from apoptosis (Socolovsky et al. (1999) Cell 98(2): 181-91; Dolznig et al. (2002) Curre Biol 12(13): 1076-1085), it was documented that transfused hemoglobin is in direct contact with bone marrow cell erythroblasts (Shum et al. (1996) Artif Cells Blood Substit Immobil Biotechnol 24(6): 655-683), therefore we thought that it was important to also evaluate the pro-apoptotic-, and anti-erythropoietic-effects of the blood substitute.

Normoxia

These experiments were carried out using the human astrocytes model as described in EXAMPLE 5. All experiments were conducted in an atmosphere of 95% air and 5% $CO_2$, representing normoxic conditions. In brief, the confluent astrocytes were incubated for approximately 18 hours in medium supplemented with hemoglobin-ATP-adenosine-GSH-based blood substitute in a final concentration of 0.1, 1.0, and 1.75 g per dL. Positive control astrocytes were incubated with medium supplemented with unmodified hemoglobin in a final concentration of 0.1, 1.0 and 1.75 g per dL. Negative control astrocytes were cultured in the absence of hemoglobin solutions that were replaced by FBS.

After treatment, the cells were subjected to evaluation by various biochemical and molecular biology methods.

The assessment of nuclear activation and DNA binding of NF-kappa B was assayed in nuclear cell extracts using TransAM™ NF-kappa B p65 transcription Factor Assay Kit (Active Motif, Carlsbad, Calif.). This method is the first ELISA-based method to detect and quantify NF-kappa B activation, that contains a 96-well plate on which there is an immobilized oligonucleotide containing the NF-kappa B consensus site (5'-GGGACTTTCC-3'). In this study, the active form of NF-kappa B, a p65 heterodimer that was present in nuclear extracts was subjected for incubation with this oligonucleotide. The nuclear extracts were obtained from living cells using complete lysis buffer that contained DTT and a protease inhibitor cocktail supplied by the manufacturer. The complete binding buffer was supplemented with DTT and herring sperm DNA. After incubation, the formed DNA-protein complex was accessible to primary antibodies, which recognized an epitope on p65. The DNA-protein complex was accessible to primary antibodies only when NF-kappa B was activated and bound to DNA. This reaction was then recognized with HRP-conjugated secondary antibodies against p65, and developed using a benzidine derivative and hydrogen peroxide. The reaction was read at 450 run using a microplate reader, Bio-Rad Model 3550-UV. Results were expressed in OD at 450 nm per 2.5 µg of whole-cell extract. The HeLa whole-cell extracts, provided by the manufacturer, were used as a positive control for NF-kappa B activation and DNA binding.

Assessment of production of pro-inflammatory cytokines with anti-erythropoietic activities (TNF-alpha and TGF-beta 1), was measured with commercially available ELISA kits.

TNF-alpha was assayed using a TNF-alpha human EIA Kit (Cayman Chemical, Ann Arbor, Mich.). This assay is based on a double-antibody 'sandwich' technique with a monoclonal antibody for human TNF-alpha. This antibody coated on the microtriter plate bound any human TNF-alpha introduced into the well. Then acetylcholnesterase (AchE):Fab' Conjugate was added to the well which selectively bound to the epitope of the human TNF-alpha molecule. The 'sandwich' is immobilized on the plate, and excess of the reagents were washed away. The concentration of the analyte was determined by measuring the enzymatic activity of the AchE with Ellman's Reagent and measured spectrophotometrically with a microplate reader (Bio-Rad Model 3550-UV). Results were expressed in pg per mL.

TGF-beta 1 was measured with Human TGF-beta 1 Quantikine Immunoassay for determination of activated human TGF-beta 1 concentration in cell culture supernate, serum and plasma (R&D Systems). In this study latent TGF-beta 1 in cell culture supernates was transferred into the immunoreactive form by acid activation and neutralization. Then, TGF-beta 1 was assayed using a microplate with a immobilized TGF-beta soluble receptor. After incubation and washing, the secondary antibody-enzyme reagent was added which with substrate developed a color in proportion to the amount of TGF-beta 1 bound in the initial step. The TGF-beta 1 concentration was expressed in pg per mL.

Apoptosis. In this study, the astrocytes grown on coverslips and exposed to the hemoglobin-ATP-adenosine-GSH-based blood substitute were evaluated for early and late apoptotic events using Annexin V-FITC and propidium iodide fluorescent probes, respectively (Sigma Chemical). Annexin V-FITC is a probe that binds to phosphatidylserine and is detected as green fluorescence. Propidium iodide binds to cellular DNA and produces red fluorescence. In the early stages of apoptosis, the loss of phospholipid asymmetry results in the translocation of phosphatidylserine, which is normally found on the internal part of the membrane, to the external portion of the membrane. Therefore, if the phosphatidyl serine becomes available on the outside of the membrane, Annexin binds to it, identifying the beginning of the apoptotic process. On the contrary, the progression of apoptosis that results in the fragmentization of the cellular DNA is detected with propidium iodide. The results were evaluated with the fluorescence microscope.

Hypoxia

Also in Example 6, hypoxic conditions (1.5% $O_2$, 93.5% $N_2$, and 5% $CO_2$) were achieved in a humidified variable aerobic workstation.

The confluent astrocytes, cultured as above, were exposed to hypoxia (1.5% $O_2$) for approximately 18 hours in the presence of pre-equilibrated medium supplemented with hemoglobin-ATP-adenosine-GSH-based blood substitute in a final concentration of 0.1, 1.0, and 1.75 g per dL. Positive control astrocytes were incubated with pre-equilibrated medium supplemented with unmodified hemoglobin in a final concentration of 0.1, 1.0 and 1.75 g per dL. Negative control astrocytes were cultured in the absence of hemoglobin solutions that were replaced by FBS.

As above, all procedures were carried out in the dark in an atmosphere of 1.5% $O_2$, 95.5% $N_2$ and 5% $CO_2$, representing hypoxic conditions. After the exposure, the cells were evaluated as above for:

1) nuclear activation and DNA binding of NF-kappa B which was assayed in nuclear cell extracts using the TransAM™ NF-kappa B p65 transcription Factor Assay Kit (Active Motif), as described above, 2) production of pro-inflammatory cytokines with anti-erythropoietic activities (TNF-alpha and TGF-beta 1, using commercially available ELISA kits, as described above, and 3) early and late apoptosis, as described above.

6.6.2. Anti-Inflammatory Effects

TABLE 5

| TGF-beta 1 (pg/mL) | HYPOXIA | | | NORMOXIA | | | |
| --- | --- | --- | --- | --- | --- | --- | --- |
| | M ± SD | Significance Cont. vs. Exp | Significance Between Exp Groups | M ± SD | Significance Cont. vs. Exp | Significance Between Exp Groups | Significance HYP. vs. NORM |
| CONTROL | 202.7 ± 44.4 | — | | 117.7 ± 47.9 | — | | $P < 0.05$ |
| Unmod. Hb 0.1 g/dL | 204.6 ± 75.4 | N.S. | — | 245.7 ± 26.59 | $P < 0.01$ | — | N.S. |
| Unmod. Hb 1.0 g/dL | 336.8 ± 85.5 | $P < 0.05$ | — | 345.5 ± 50.4 | $P < 0.01$ | — | N.S. |
| Unmod. Hb 1.75 g/dL | 446.1 ± 81.3 | $P < 0.01$ | — | 573.1 ± 77.8 | $P < 0.001$ | — | $P < 0.05$ |
| Blood Subst. 0.1 g/dL | 102.9 ± 59.3 | $P < 0.05$ | $P < 0.05$ | 153.8 ± 65.9 | N.S. | $P < 0.05$ | N.S. |
| Blood Subst. 1.0 g/dL | 164.2 ± 59.4 | N.S. | $P < 0.01$ | 147.5 ± 58.4 | N.S. | $P < 0.01$ | N.S. |
| Blood Subst. 1.75 g/dL | 201.36 ± 54.0 | N.S. | $P < 0.001$ | 182.9 ± 65.9 | N.S. | $P < 0.001$ | N.S. |

TABLE 6

| TNF-alpha (pg/mL) | HYPOXIA | | | NORMOXIA | | | |
| --- | --- | --- | --- | --- | --- | --- | --- |
| | M ± SD | Significance Cont. vs. Exp | Significance Between Exp Groups | M ± SD | Significance Cont. vs. Exp | Significance Between Exp Groups | Significance HYP. vs. NORM |
| CONTROL | 6.35 ± 3.66 | — | | 5.47 ± 3.31 | — | | N.S. |
| Unmod. Hb 0.1 g/dL | 4.87 ± 2.82 | N.S. | — | 6.46 ± 3.51 | N.S. | — | N.S. |
| Unmod. Hb 1.0 g/dL | 5.42 ± 3.13 | N.S. | — | 5.65 ± 3.26 | N.S. | — | N.S. |
| Unmod. Hb 1.75 g/dL | 27.04 ± 5.06 | $P < 0.01$ | — | 14.92 ± 2.69 | $P < 0.05$ | — | $P < 0.05$ |
| Blood Subst. 0.1 g/dL | 5.61 ± 3.24 | N.S. | N.S. | 5.55 ± 3.20 | N.S. | N.S. | N.S. |
| Blood Subst. 1.0 g/dL | 4.72 ± 2.74 | N.S. | N.S. | 5.30 ± 3.06 | N.S. | N.S. | N.S. |
| Blood Subst. 1.75 g/dL | 5.39 ± 3.12 | N.S. | $P < 0.01$ | 5.27 ± 3.04 | N.S. | $P < 0.05$ | N.S. |

Figure 7:
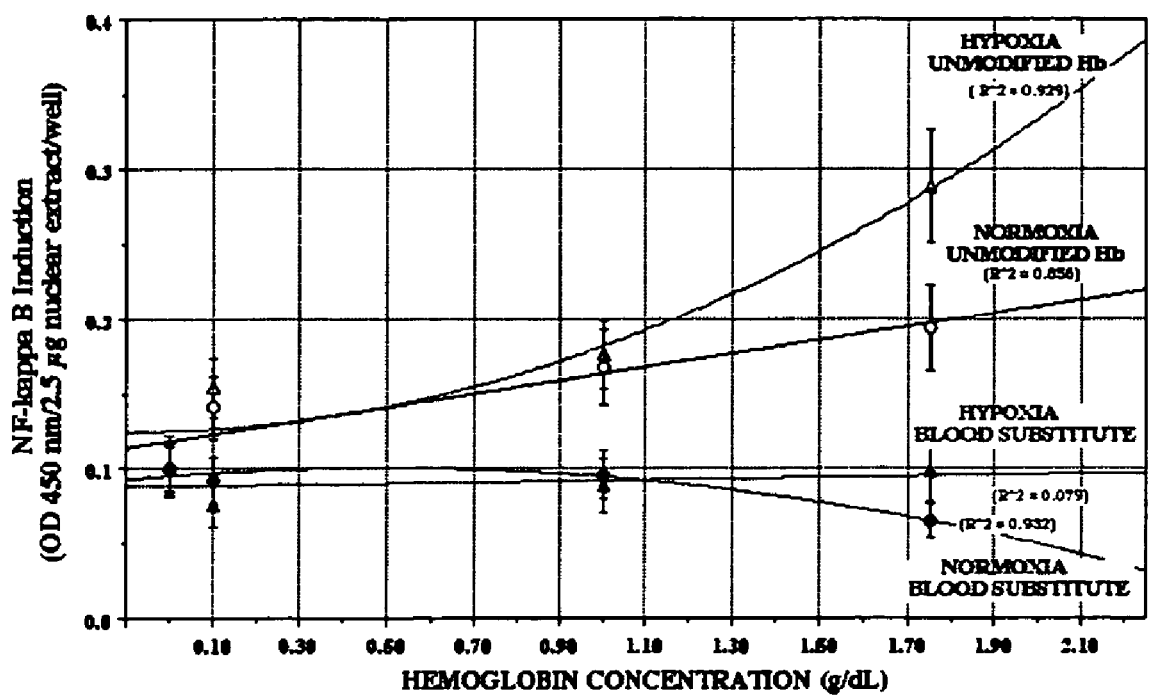
FIG. 7 shows the effect of hemoglobin-ATP-adenosine-GSH-based blood substitute and unmodified hemoglobin solution in concentrations of 0.1, 1.0 and 1.75 g per dL on activation of anti-erythropoietic NF-kappa B in human astrocytes under hypoxic and normoxic conditions.

As seen in FIG. 7, the hemoglobin-ATP-adenosine-GSH-based blood substitute has inhibited NF-kappa B activation at all tested concentrations and oxygen levels. On the contrary, unmodified hemoglobin activates NF-kappa B induction in a dose dependent manner. This effect was more prone in the normoxic condition.

As seen in TABS. 5 and 6, the hemoglobin-ATP-adenosine-GSH-based blood substitute in a dose dependent manner, at both tested oxygen conditions, inhibited the formation of TGF-beta 1 and did not increase the production of TNF-alpha, which are the most potent anti-erythropoietic agents. This effect can be linked with inability of this blood substitute to induce NF-kappa B.

The unmodified hemoglobin solution, however, increased the production of both anti-erythropoietic agents, TGF-beta 1 and TNF-alpha, especially when given in higher concentrations (1 and 1.75 g per dL).

The experiments described in Example 6, illustrate that the hemoglobin-ATP-adenosine-GSH-based blood substitute has anti-inflammatory potential, while the unmodified hemoglobin has pro-inflammatory properties.

Since high activity of the NF-kappa B pathway is involved in the suppression of erythroid-specific genes while TGF-beta 1 blocks the differentiation of erythroid progenitor, and TNF-alpha inhibits the HIF-1 alpha binding to the EPO gene, it is reasonable to suggest that anti-inflammatory properties of the hemoglobin-ATP-adenosine-GSH-based blood substitute could serve as an erythropoietic factor.

6.6.3. Anti-Apoptotic Effects

Results/Conclusions

The control astrocytes under the normoxic condition did not show any pro-apoptotic responses. Fluorescence analysis revealed a lack of Annexin's surface binding and nuclear accumulation of propidium iodide, which can be interpreted as the absence of early and late apoptotic events. Hypoxia resulted in the accumulation of Annexin V-FITC on the surface of astrocytes. This effect is an indication of a translocation of phosphatidylserine to the external portion of the membrane, which occurs, in early apoptosis.

The treatment of astrocytes with unmodified hemoglobin resulted in early apoptosis in normoxic conditions and advanced apoptosis in hypoxia. The accumulation of propidium iodide in hypoxic astrocytes exposed to the unmodified hemoglobin solution was the result of the compromised plasma membrane and the fragmentarization of DNA. Unmodified hemoglobin in higher concentrations introduced more devastating effects.

The hemoglobin-ATP-adenosine-GSH-based blood substitute did not induce an apoptotic reaction at any tested concentration or oxygen content.

Since a principal function of EPO as a pro-erythropoietic agent is to protect pro-erythroblasts from apoptosis, the hemoglobin-ATP-adenosine-GSH-based blood substitute, which accelerates HIF-1 alpha mediated production of EPO, will not interfere with EPOs function. On the contrary, the unmodified hemoglobin solution with high pro-apoptotic potential can serve as an anti-erythropoietic agent, especially in larger concentrations.

6.6.4. General Conclusions

The chemical/pharmacological modification of hemoglobin with ATP, adenosine and GSH, as described in U.S. Pat. No. 5,439,882, resulted in an improved blood substitute product which has vasodilatory activity and good tissue oxygenation ability, and erythropoietic activity through HIF-1 alpha stabilization and subsequent EPO induction. The anti-inflammatory and anti-apoptotic potential of this blood substitute product accelerates the erythropoietic responses.

This blood substitute product by expressing pro-erythropoietic potential at high concentrations (grams/kg body weight) can serve as initial therapy to maintain tissue oxygenation and secondary' therapy to normalize the hematocrit through stimulation of patients' erythropoietic responses.

Hemoglobin-ATP-adenosine-GSH-based blood substitute therapy does not require expensive recombinant EPO support.

6.7. (Prophetic) Example Seven—Treatment of Acute Blood Loss in Subjects 6.7.1. Experimental Design No. 1

Human subjects diagnosed with acute blood loss anemia are divided into group A and B, with an equal number of men and women, adults and children.

The subjects in group A are treated with a blood substitute of the present invention over a period of time, and the subjects in group B are given a placebo blood substitute over the same period of time.

During and after the treatment period, the subjects' hematrocrit levels, hemoglobin levels, circulating erythropoietin levels, and hemodynamic parameters are measured and compared.

6.7.2. Experimental Design No. 2

A first group of human subjects experiencing blood loss greater than 33% blood volume during surgery are given a blood substitute of the present invention. A second group of human subjects experiencing blood loss greater than 33% blood volume during surgery are given conventional blood transfusion. Both groups have an equal number of men and women, adults and children.

During and after the surgery, the subjects' hematrocrit levels, hemoglobin levels, circulating erythropoietin levels, and hemodynamic parameters are measured and compared.

6.7.3. Experimental Design No. 3

A first group of human subjects experiencing blood loss greater than 33% blood volume from trauma (e.g., gunshot wound, car accident) are given a blood substitute of the present invention. A second group of human subjects experiencing blood loss greater than 33% blood volume from the same type of trauma are given conventional blood transfusion. Both groups have an equal number of men and women, adults and children.

Afterwards, the subjects' hematrocrit levels, hemoglobin levels, circulating erythropoietin levels, and hemodynamic parameters are measured and compared.

The present invention is not to be limited in scope by the specific embodiments described herein. Indeed, various modifications of the present invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention claimed is:

1. A method for treating severe acute blood loss anemia in a subject, comprising administering to the subject in need thereof a cross-linked hemoglobin blood substitute in an amount effective to elevate blood volume and counteract hypoxia associated with the severe acute blood loss anemia in the subject, wherein the cross-linked hemoglobin blood substitute
   (i) when tested in a cell culture under normoxic conditions, induces expression of erythropoietin; or
   (ii) induces erythropoiesis under normoxic conditions as measured by a decrease in the doubling time of the subject's hematocrit or hemoglobin; or
   (iii) induces erythropoiesis under normoxic conditions as measured by an increase in the subject's circulating erythropoietin level,
   wherein the cross-linked hemoglobin blood substitute, when tested in a cell culture, stabilizes HIF-1 alpha expression.

2. A method for treating severe acute blood loss anemia in a subject, comprising administering to the subject in need thereof a cross-linked hemoglobin in an amount effective to treat the severe acute blood loss anemia in the subject, wherein the cross-linked hemoglobin comprises a hemoglobin that is
   (i) cross-linked intramolecularly with periodate-oxidized ATP; and
   (ii) cross-linked intermolecularly with periodate-oxidized adenosine; and
   (iii) conjugated with reduced glutathione,
   wherein the cross-linked hemoglobin, when tested in a cell culture, stabilizes HIF-1 alpha expression.

3. The method of claim 2, wherein the hemoglobin and periodate-oxidized ATP in the cross-linked hemoglobin are at a molar ratio of 1:1 to 1:3.

4. The method of claim 2, wherein the hemoglobin and periodate-oxidized adenosine in the cross-linked hemoglobin are at a molar ratio of 1:1 to 1:10.

5. The method of claim 2, wherein the hemoglobin and reduced glutathione in the cross-linked hemoglobin are at a molar ratio of 1:1 to 1:20.

6. A method for treating severe acute blood loss that occurs during surgery in a subject, comprising administering to the subject in need thereof a cross-linked hemoglobin blood substitute in an amount effective to elevate blood volume and counteract hypoxia associated with the severe acute blood loss anemia in the subject, wherein the cross-linked hemoglobin blood substitute
   (i) when tested in a cell culture under normoxic conditions, induces expression of erythropoietin; or
   (ii) induces erythropoiesis under normoxic conditions as measured by a decrease in the doubling time of the subject's hematocrit or hemoglobin; or
   (iii) induces erythropoiesis under normoxic conditions as measured by an increase in the subject's circulating erythropoietin level,
   wherein the cross-linked hemoglobin blood substitute, when tested in a cell culture, stabilizes HIF-1 alpha expression.

7. A method for treating severe acute blood loss that occurs during surgery in a subject, comprising administering to the subject in need thereof a cross-linked hemoglobin in an amount effective to treat the severe acute blood loss anemia in the subject, wherein the cross-linked hemoglobin comprises a hemoglobin that is
- (i) cross-linked intramolecularly with periodate-oxidized ATP; and
- (ii) cross-linked intermolecularly with periodate-oxidized adenosine; and
- (iii) conjugated with reduced glutathione, wherein the cross-linked hemoglobin, when tested in a cell culture, stabilizes HIF-1 alpha expression.

8. The method of claim 7, wherein the hemoglobin and periodate-oxidized ATP in the cross-linked hemoglobin are at a molar ratio of 1:1 to 1:3.

9. The method of claim 7, wherein the hemoglobin and periodate-oxidized adenosine in the cross-linked hemoglobin are at a molar ratio of 1:1 to 1:10.

10. The method of claim 7, wherein the hemoglobin and reduced glutathione in the cross-linked hemoglobin are at a molar ratio of 1:1 to 1:20.

11. The method of claim 6 or 7, wherein the surgery is an elective surgery.

12. A method for treating severe blood loss from trauma in a subject, comprising administering to the subject in need thereof a cross-linked hemoglobin blood substitute in an amount effective to elevate blood volume and counteract hypoxia associated with the severe acute blood loss anemia in the subject, wherein the cross-linked hemoglobin blood substitute
- (i) when tested in a cell culture under normoxic conditions, induces expression of erythropoietin; or
- (ii) induces erythropoiesis under normoxic conditions as measured by a decrease in the doubling time of the subject's hematocrit or hemoglobin; or
- (iii) induces erythropoiesis under normoxic conditions as measured by an increase in the subject's circulating erythropoietin level, wherein the cross-linked hemoglobin blood substitute, when tested in a cell culture, stabilizes HIF-1 alpha expression.

13. A method for treating severe blood loss from trauma in a subject, comprising administering to the subject in need thereof a cross-linked hemoglobin in an amount effective to treat the severe acute blood loss anemia in the subject, wherein the cross-linked hemoglobin comprises a hemoglobin that is
- (i) cross-linked intramolecularly with periodate-oxidized ATP; and
- (ii) cross-linked intermolecularly with periodate-oxidized adenosine; and
- (iii) conjugated with reduced glutathione, wherein the cross-linked hemoglobin, when tested in a cell culture, stabilizes HIF-1 alpha expression.

14. The method of claim 13, wherein the hemoglobin and periodate-oxidized ATP in the cross-linked hemoglobin are at a molar ratio of 1:1 to 1:3.

15. The method of claim 13, wherein the hemoglobin and periodate-oxidized adenosine in the cross-linked hemoglobin are at a molar ratio of 1:1 to 1:10.

16. The method of claim 13, wherein the hemoglobin and reduced glutathione in the cross-linked hemoglobin are at a molar ratio of 1:1 to 1:20.

17. The method of claim 1, 2, 6, 7, 12 or 13, wherein the subject has greater than 33% blood loss.

18. The method of claim 1, 2, 6, 7, 12 or 13, wherein the subject is a human.

19. The method of claim 18, wherein the subject has less than 7 g/dL hemoglobin.

20. The method of claim 1, 2, 6, 7, 12 or 13, comprising administering to the subject in need thereof the blood substitute.

* * * * *